(12) United States Patent
Brucker et al.

(10) Patent No.: US 11,298,203 B2
(45) Date of Patent: Apr. 12, 2022

(54) SYSTEM AND METHOD FOR DEFLECTION OF A BODY LUMEN

(71) Applicant: Innovations in Medicine, LLC, Minnetonka, MN (US)

(72) Inventors: Gregory G. Brucker, Minneapolis, MN (US); Steven D. Savage, Lake Havasu City, AZ (US)

(73) Assignee: Innovations in Medicine, LLC, Minnetonka, MN (US)

( * ) Notice: Subject to any disclaimer, the term of this patent is extended or adjusted under 35 U.S.C. 154(b) by 379 days.

(21) Appl. No.: 16/462,377

(22) PCT Filed: Nov. 23, 2017

(86) PCT No.: PCT/US2017/063171
§ 371 (c)(1),
(2) Date: May 20, 2019

(87) PCT Pub. No.: WO2018/098388
PCT Pub. Date: May 31, 2018

(65) Prior Publication Data
US 2019/0314109 A1 Oct. 17, 2019

Related U.S. Application Data

(60) Provisional application No. 62/426,223, filed on Nov. 23, 2016.

(51) Int. Cl.
*A61B 90/00* (2016.01)
*A61B 18/00* (2006.01)
(Continued)

(52) U.S. Cl.
CPC .............. *A61B 90/04* (2016.02); *A61B 18/00* (2013.01); *A61M 25/1002* (2013.01);
(Continued)

(58) Field of Classification Search
CPC ............ A61B 90/04; A61B 2090/0427; A61B 17/0218; A61M 25/0147; A61M 2025/1072
See application file for complete search history.

(56) References Cited

U.S. PATENT DOCUMENTS

| 4,734,093 A | 3/1988 | Bonello et al. |
| 4,983,167 A | 1/1991 | Sahota |

(Continued)

FOREIGN PATENT DOCUMENTS

| JP | 1993507212 | 10/1993 |
| WO | WO_1991011213 | 8/1991 |

(Continued)

OTHER PUBLICATIONS

European Patent Office, "EPO Supplementary Search Report/Written Opinion for related application EP 17873942.1, dated Aug. 4, 2020, 6 pages.".

(Continued)

*Primary Examiner* — Carrie R Dorna
(74) *Attorney, Agent, or Firm* — Charles A. Lemaire; Jonathan M. Rixen; Lemaire Patent Law Firm, P.L.L.C.

(57) ABSTRACT

A positioning device configured for introduction within a body lumen. Some embodiments include a catheter shaft with a longitudinal axis; an expandable element coupled along a length of the shaft, the expandable element being substantially thin and flexible in an unexpanded state and exerting a gentle outward force in an expanded state; and a deflection mechanism located within the shaft, wherein the deflection mechanism is flexible when in a non-deflected state and wherein, in the deflected state, the deflection curves in a predetermined lateral direction such that the positioning device laterally deflects the body lumen. In some embodiments, the deflection is a lateral curve that moves the (Continued)

body lumen away from a surgical site, such as a cardiac ablation site.

22 Claims, 14 Drawing Sheets

(51) Int. Cl.
 *A61M 25/10* (2013.01)
 *A61M 25/01* (2006.01)
 *A61M 25/09* (2006.01)

(52) U.S. Cl.
 CPC .............. *A61M 25/1011* (2013.01); *A61B 2018/00351* (2013.01); *A61B 2018/00577* (2013.01); *A61B 2090/0427* (2016.02); *A61M 25/0108* (2013.01); *A61M 25/0147* (2013.01); *A61M 25/09* (2013.01)

(56) References Cited

U.S. PATENT DOCUMENTS

| | | | |
|---|---|---|---|
| 5,045,061 A | 9/1991 | Seifert et al. | |
| 5,195,968 A | 3/1993 | Lundquist et al. | |
| 5,531,776 A | 7/1996 | Ward et al. | |
| 5,820,591 A | 10/1998 | Thompson et al. | |
| 6,067,990 A | 5/2000 | Kieturakis | |
| 6,733,500 B2 | 5/2004 | Kelley et al. | |
| 7,621,908 B2 | 11/2009 | Miller | |
| 8,273,016 B2 | 9/2012 | O'Sullivan | |
| 8,454,588 B2 | 6/2013 | Rieker et al. | |
| 8,529,443 B2 | 9/2013 | Maloney | |
| 9,119,927 B1 | 9/2015 | Ratterree et al. | |
| 9,668,720 B2 | 6/2017 | Kasic | |
| 9,931,108 B2 | 4/2018 | Miller | |
| 9,937,329 B2 | 4/2018 | Niazi | |
| 10,307,520 B2 | 6/2019 | Oza et al. | |
| 2011/0034936 A1* | 2/2011 | Maloney | A61M 16/0486 606/108 |
| 2011/0082188 A1 | 4/2011 | Chakravarti | |
| 2011/0082488 A1* | 4/2011 | Niazi | A61M 25/1002 606/192 |
| 2014/0094839 A1 | 4/2014 | Nimkar et al. | |
| 2015/0245829 A1 | 9/2015 | Fojtik | |
| 2017/0105715 A1 | 4/2017 | Kasic | |
| 2017/0360503 A1* | 12/2017 | Miller | A61B 18/1492 |
| 2019/0269834 A1 | 9/2019 | Oza et al. | |

FOREIGN PATENT DOCUMENTS

WO WO_2015153595 A1 10/2015
WO WO_2016139552 9/2016

OTHER PUBLICATIONS

"Office Action for related Japanese Patent Application 2019-526586, dated Nov. 30, 2021, 7 pages (JPO machine translation)".

* cited by examiner

*FIG. 2A1*
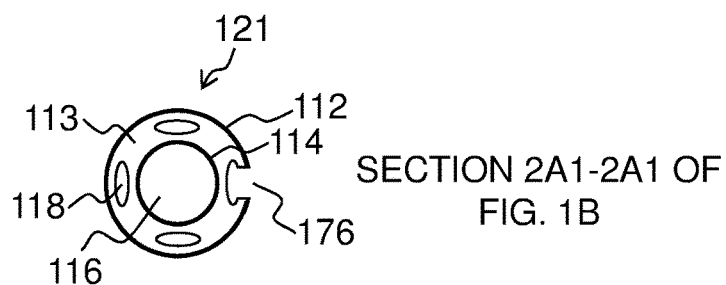
SECTION 2A1-2A1 OF FIG. 1B
*FIG. 2A2*
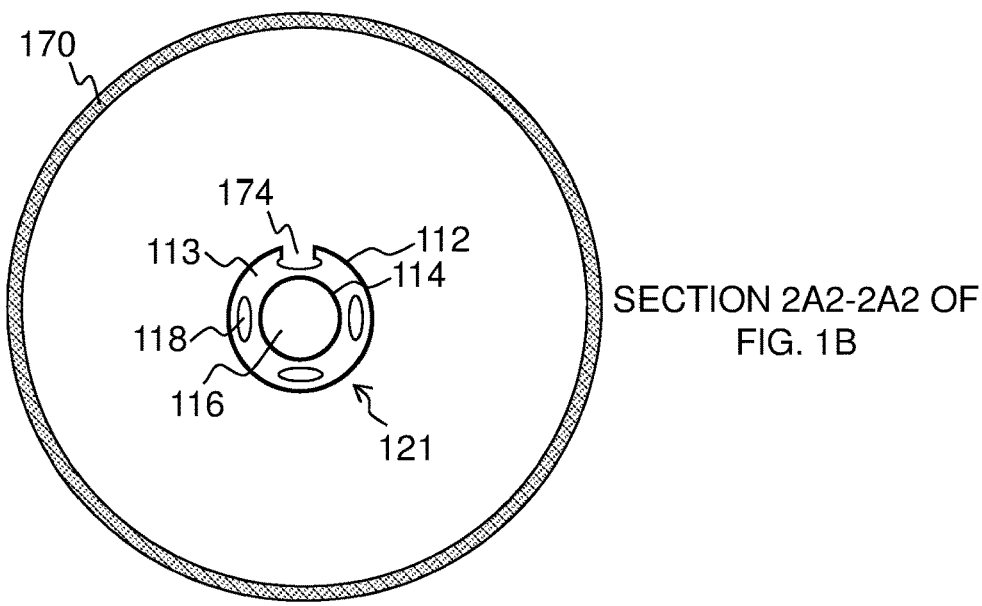
SECTION 2A2-2A2 OF FIG. 1B
*FIG. 2B*
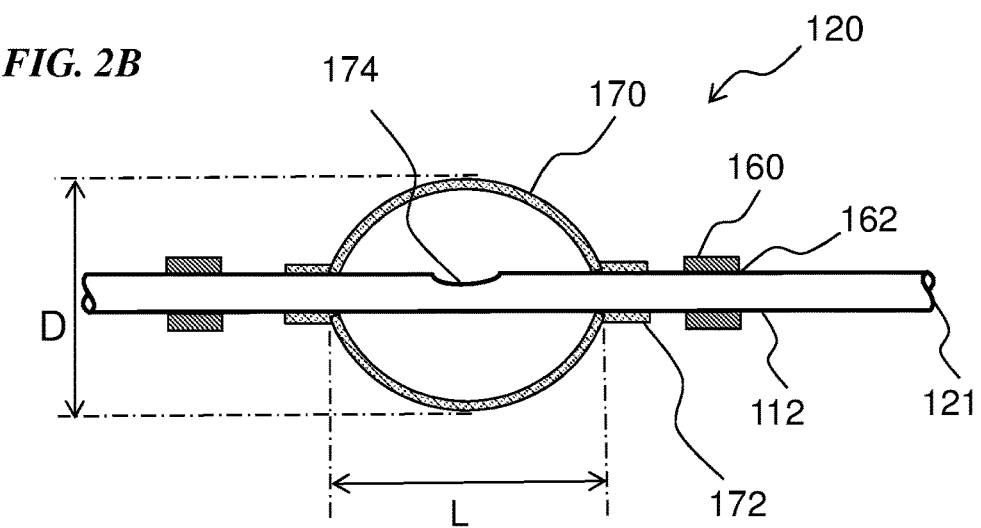
SECTION 2B-2B OF FIG. 1B FIG. 3B
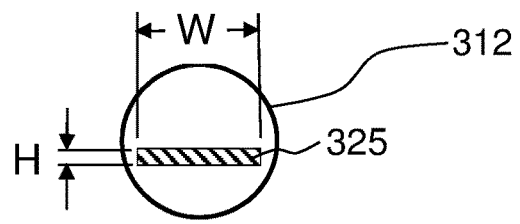
SECTION 3B-3B OF
FIG. 3A
FIG. 3C
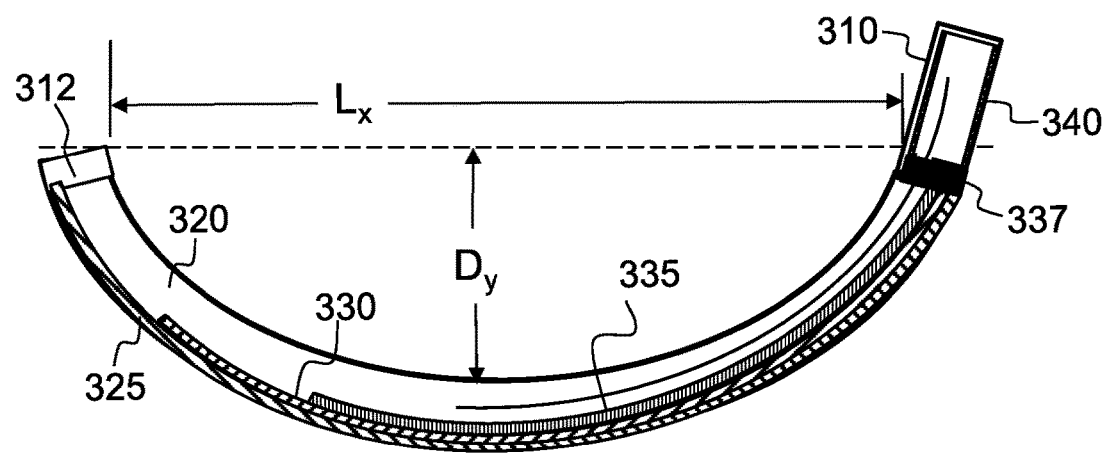

FIG. 3H
FIG. 3i
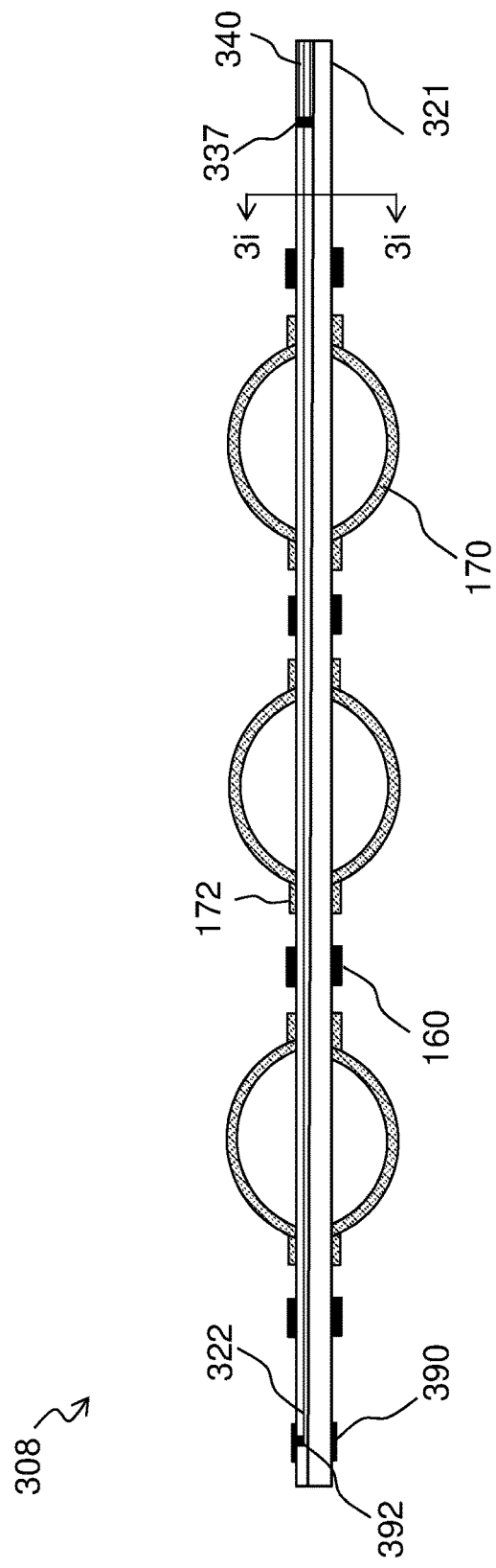
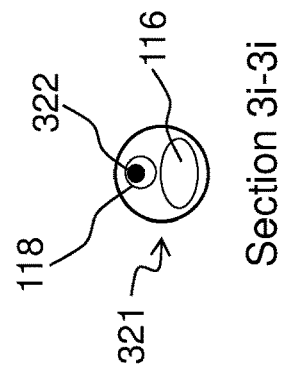

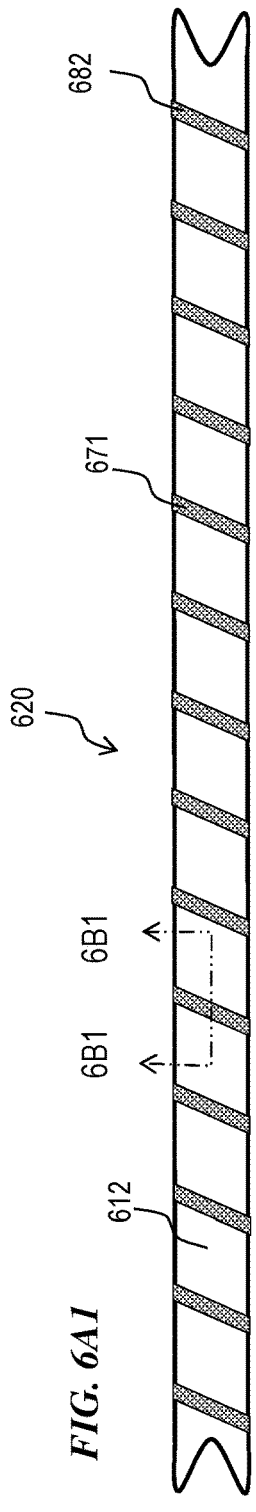
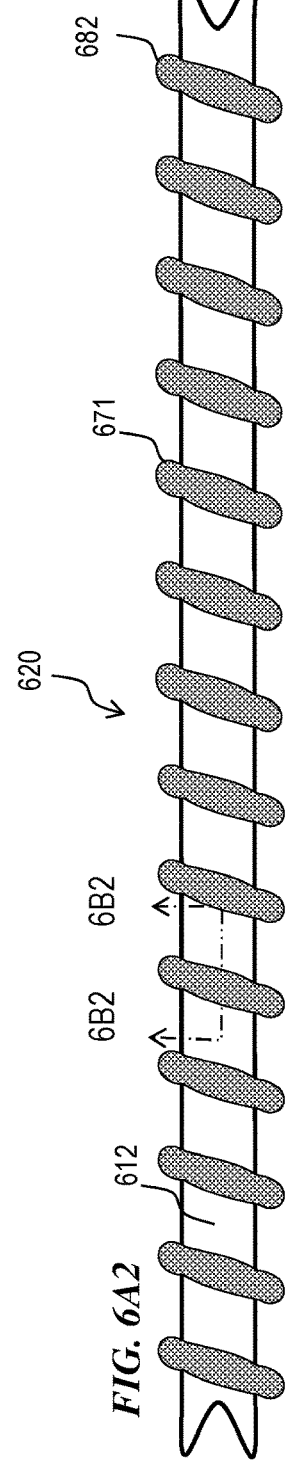
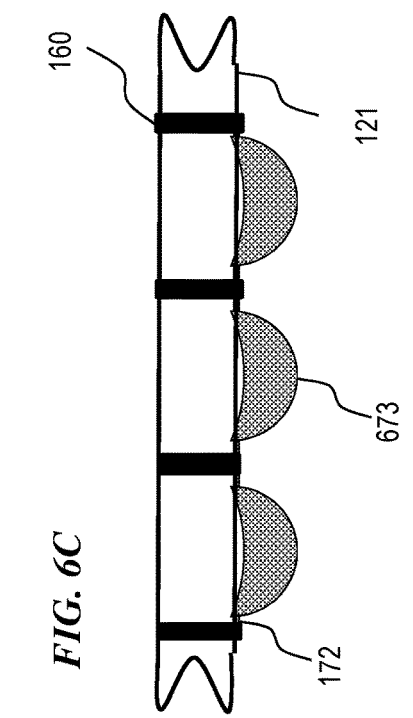
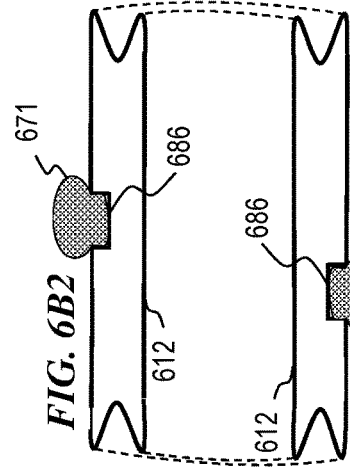
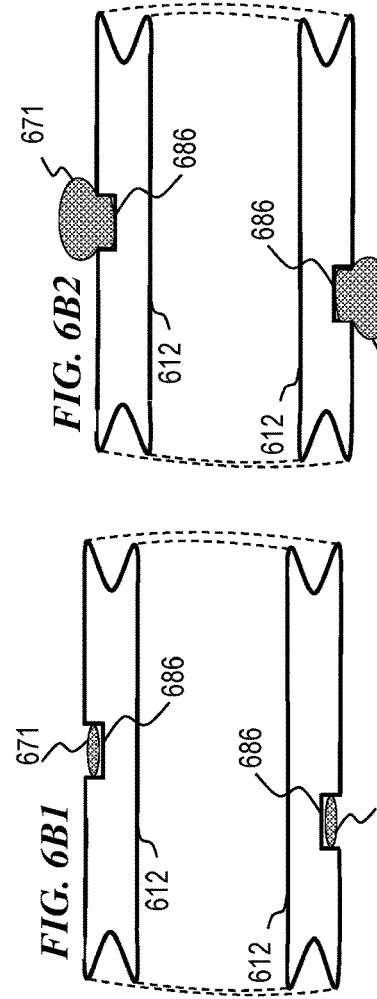

FIG. 6D1
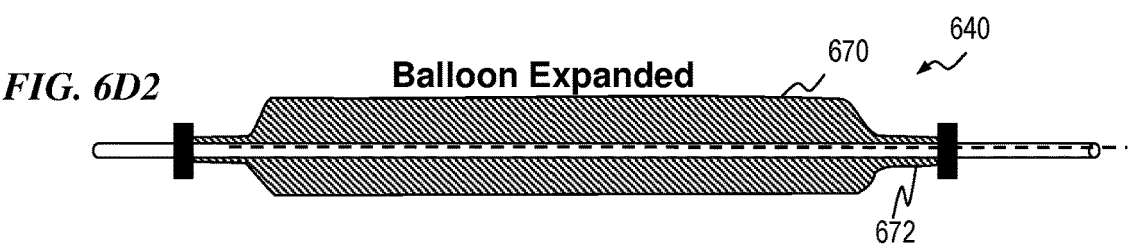
FIG. 6D2
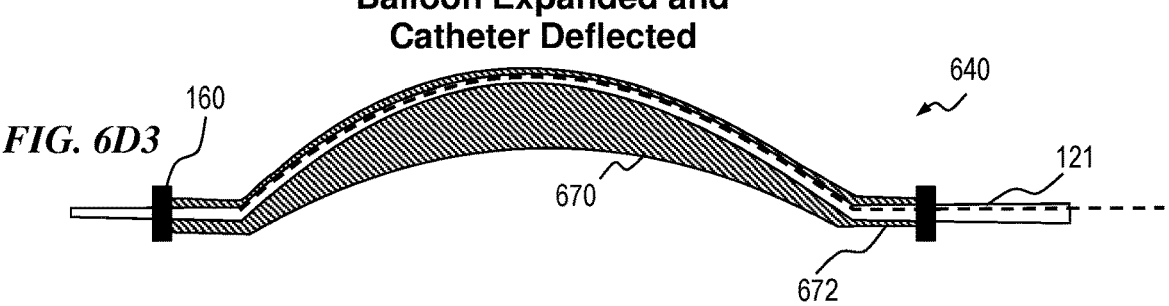
FIG. 6D3
FIG. 6D4
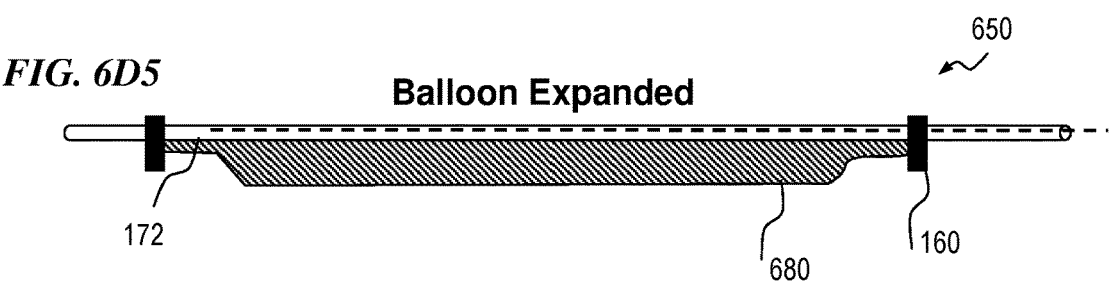
FIG. 6D5
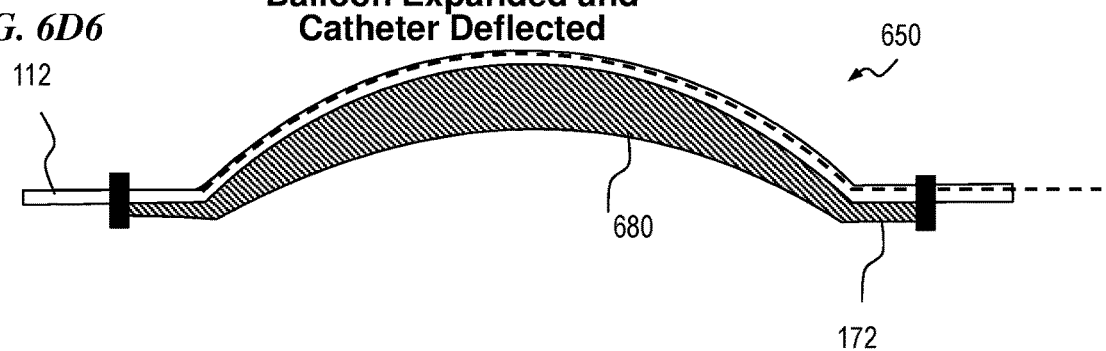
FIG. 6D6

SYSTEM AND METHOD FOR DEFLECTION OF A BODY LUMEN

CROSS-REFERENCE TO RELATED APPLICATIONS

This application is a national-phase filing of, and claims priority benefit of, PCT Patent Application No. PCT/US2017/063171, filed Nov. 23, 2017 by Gregory G. Brucker, et al., and titled "System and method for deflection of a body lumen," which claims priority benefit, including under 35 U.S.C. § 119(e), of U.S. Provisional Patent Application No. 62/426,223, filed Nov. 23, 2016 by Gregory G. Brucker, et al., and titled "System and method for deflection of a body lumen," each of which is incorporated herein by reference in its entirety.

FIELD OF THE INVENTION

Embodiments of the present invention relate generally to a catheter for deflection of a lumen within a body cavity for the purpose of repositioning a body lumen to substantially reduce or eliminate unintended damage to a bodily organ during delivery of therapy, such as moving the esophagus away from the heart during an ablation procedure for treatment of atrial fibrillation to minimize potential for formation of an atrial-esophageal fistula. The present invention includes an expansion catheter for enlarging a body lumen to reduce its elasticity and a deflection mechanism attached to or located within the expansion catheter to move the body lumen from its natural position within the body.

BACKGROUND OF THE INVENTION

Devices for deflection of a body lumen can be classified by the mechanism by which deflection occurs, namely: mechanical or expandable. Mechanical deflection uses a pre-curved element such as a stylet inserted into a flexible tube placed within a body lumen to reposition a portion of the body lumen within a body cavity. Alternatively, a wire can be housed within a flexible tube and wire tension used to curve the tube and move a body lumen a desired distance. Expandable deflection uses an element, for example a balloon, which contains a predefined curvature such that upon expansion from a smaller diameter to a larger diameter the body lumen is repositioned by virtue of the curvature of the expanded element. Both deflection mechanisms have limited clinical benefit for repositioning a body lumen within a body cavity, primarily due to the elasticity of most body lumens. For example, for treatment of atrial fibrillation using cardiac ablation therapies, it is often desirable to reposition the esophagus in regions near the posterior wall of the left atrium to prevent the formation of an atrial-esophageal fistula which can be fatal or to prevent periesophageal vagus plexus injury. The diameter and elasticity of the esophagus has limited the ability of aforementioned deflection methods to adequately reposition the esophagus to reduce clinical risk, thereby limiting their clinical value.

For mechanical devices that typically use tubes and a deflection means contained therein, the diameter of the device is generally smaller than the lumen into which it is inserted. Because of the diameter difference between the device and the body lumen, the initial deflection of a mechanical device first moves to engage some aspect of a luminal wall which then, because of the concentrated force loadings on the luminal wall and elasticity of the body lumen, changes the lateral cross-sectional profile of the body lumen from circular to ellipsoidal with an increasingly higher aspect ratio. Effectively, even though there is significant lateral movement of the device, the movement of the centerline of the body lumen relative to other body structures is substantially reduced. Larger-diameter tubes can be used to minimize these aforementioned effects, but, as devices become larger, they also become stiffer, making insertion more complicated and risk of collateral tissue damage higher. For example, in esophageal applications, deflection devices are normally inserted either through the nose or throat, which limits device diameters to 3 mm (0.118 inch) and 9 mm (0.354 inch), respectively, while the diameter of the esophagus ranges from 15 to 30 mm (0.591 to 1.181 inch). In general this has limited lateral movement of the esophagus to about 2.0 cm (0.787 inch), with a more desirable range being 3.0 to 4.0 cm (1.18 to 1.57 inch).

For expandable devices which have an element which enlarges to approximately the diameter of the body lumen, the expandable element generally has a preset curvature when enlarged. During use, the pre-curved element first expands to engage a body lumen and then, upon continued expansion, deflects the body lumen from its normal pathway through a body cavity. The most common implementations of this type of deflection mechanism are pre-shaped balloons or curved wire meshes. The advantage of these devices is they maintain the diameter and circularity of the body lumen so that curvature of the device results in more movement of the centerline of the body lumen from its normal pathway. The disadvantage of expandable devices is the higher forces required for deflection, which translates into higher-pressure balloons or thicker mesh wires, resulting in stiffer devices and larger diameter crossing profiles in their unexpanded state, both possibly damaging to the body lumen and clinically undesirable.

In addition to the aforementioned disadvantages, both mechanical deflection devices and expandable devices require additional steps when repositioning the deflection device within a body lumen. Since the deflection mechanism is an integral part of the device, the deflection device must be returned to its neutral state before repositioning within a body lumen. At a minimum, this requires additional procedural time, which potentially exposes the patient to additional risk during manipulation of the deflection device.

U.S. Pat. No. 7,621,908, issued Nov. 24, 2009, titled "Catheter for Manipulation of the Esophagus" by Steven W. Miller, which is incorporated herein by reference in its entirety, describes an esophageal catheter for displacing and fixing the position of the esophagus in relation to the atrium of the heart which is composed of a long flexible tube to be inserted into the esophagus. A control wire is associated with the tube to change the shape of the catheter and displace the esophagus relative to the heart to reduce the risk of an esophageal fistula resulting from atrial RF ablation.

U.S. Pat. No. 8,529,443, issued Sep. 10, 2013, titled "Nasogastric Tube for Use during an Ablation Procedure" by James D. Maloney, which is incorporated herein by reference in its entirety, describes embodiments of the present invention to provide a nasogastric tube for deflecting an esophagus during an ablation procedure. According to one embodiment, the nasogastric tube includes a flexible tube that includes at least one lumen having proximal and distal ends, and an esophageal deflector positioned within the at least one lumen and configured to be mechanically actuated to assume a curved profile so as to deflect a portion of the tube between the proximal and distal ends. The esophageal deflector is configured to deflect the portion of the tube proximate to a retrocardiac portion of the esophagus such that the retrocardiac portion of the esophagus is deflected away from an ablation site.

U.S. Pat. No. 8,273,016, issued on Sep. 25, 2012, titled "Esophageal Isolation Device" by Martin F. O'Sullivan, which is incorporated herein by reference in its entirety, describes an esophageal-isolation catheter for deflecting an esophagus of a patient away from an ablation site in the left atrium of the patient's heart. The catheter includes an elongated catheter body and a deflectable section. In one embodiment, the catheter includes a deflectable intermediate section mounted at the distal end of the catheter body and a generally straight tip section mounted at the distal end of the intermediate section. In this embodiment, the catheter includes two pull wires, one anchored proximal the other. The intermediate section deflects to form a generally C-shaped or omega-shaped (Ω-shaped) curve. In an alternative embodiment, the catheter includes a deflectable tip section mounted at the distal end of the catheter body. In this embodiment, the catheter includes only one pull wire. The tip section carries a tip electrode having an atraumatic design to prevent damage to the esophagus upon deflection.

U.S. Pat. No. 8,454,588, issued on Jun. 4, 2013, titled "Method and Apparatus to Prevent Esophageal Damage" by Gregory B. Rieker et al., which is incorporated herein by reference in its entirety, describes an apparatus for moving the esophagus which includes an elongate body having a distal tip, a controlled curvature section, and a flexible section. A handle is coupled to the flexible section to adjust the curvature of the controlled curvature section. The length of the controlled curvature section is less than the length of the thoracic portion of the esophagus. Further, a method of adjusting the curvature of the esophagus during a therapeutic procedure in a treatment area outside of the esophagus includes positioning within the esophagus an elongate body having a distal tip, a controlled curvature section, and a flexible section and adjusting the curvature of the controlled curvature section to increase the distance between the esophagus and a treatment area outside of the esophagus.

U.S. Pat. No. 9,119,927, issued Sep. 1, 2015, titled "Apparatus and Method for Intubating Humans and Non-Human Animals" by Jerry B. Ratterree et al., which is incorporated herein by reference in its entirety, describes an apparatus and a corresponding method for intubating a human or non-human animal patient. In some embodiments, the present invention is used in the field of anesthesia and emergency medicine. In some embodiments, the present invention provides an intubation tube that includes an integrated Blaine Bafflex System having a plurality of blaines for sealing the trachea, wherein the intubation tube is formed from a single material. In some embodiments, the shape and outer circumference of each blaine of the system is selected according to the desired use of the intubation tube (e.g., for intubating a pediatric patient or an adult patient or for intubating a small animal or a large animal). In some embodiments, the distance between successive blaines is selected such that, when the intubation tube is inserted into the patient and the blaines bend, none of the blaines overlap with their nearest neighbor.

U.S. Patent Publication 2011/0082488, published on Apr. 7, 2011, titled "Intra-Esophageal Balloon System" by Imran K. Niazi, which is incorporated herein by reference in its entirety, discloses a device and system for selective inflation of an inflatable body, such as a balloon, received through an oral cavity and into the esophagus of a patient. The inflatable body is operably coupled to a pressurized fluid source. The inflatable body has a relatively flexible portion and a relatively inflexible portion. When pressurized fluid is delivered to the body to inflate the body, the flexible portion expands more than the inflexible portion, resulting in asymmetrical expansion and movement of the esophagus away from the ablation site to avoid accidental injury while performing a procedure on the patient's left atrium. This movement may be opposite from or directly away from the heart or, alternatively, may be sideways relative to the heart to a location in which the esophagus is interposed between the ablation site and the phrenic nerve. The supplied fluid may be radio-opaque liquid to allow for imaging thereof to assist in positioning the balloon. The liquid may additionally be relatively cool as compared to the patient's body temperature so serve as a heat sink against heat applied to surrounding areas.

U.S. Patent Publication 2015/0245829, published on Sep. 3, 2015, titled "Expandable Device for Positioning Organs" by Shawn K. Fojtik, which is incorporated herein by reference in its entirety, discloses a positioning device configured to selectively position or otherwise manipulate one or more organs within the body of a subject. The positioning device includes a shaped expandable element that is configured to be selectively transitioned between an unexpanded, or collapsed, state and an expanded state. While in the expanded state, the expandable element repositions or otherwise manipulates an organ. Systems that include positioning devices are also disclosed, as are methods for positioning or otherwise manipulating organs.

There is a need for an improved system for deflection of a body lumen, for use in positioning the lumen for surgical procedures and other purposes.

SUMMARY OF THE INVENTION

In some embodiments, the present invention provides an apparatus for displacing a portion of a flexible target lumen, wherein the apparatus includes: a catheter shaft having a first catheter-shaft lumen within the catheter shaft, the first catheter-shaft lumen extending through at least a portion of length of the catheter shaft, a plurality of inflatable and deflatable balloons located along the catheter shaft and operably coupled to the first catheter-shaft lumen and configured to expand in diameter within the flexible target lumen to form an expanded first portion of the apparatus, and a lateral deflection mechanism operably coupled to the catheter shaft and configured to laterally deflect the expanded first portion of the apparatus while within the flexible target lumen in order to laterally deflect the flexible target lumen.

Some embodiments of the current invention for manipulation of a bodily lumen are designed to combine a mechanical approach with an expandable element approach to obtain the benefits of more reliable positioning, larger body-lumen deflection and easier clinical use. These benefits are derived from three features that collectively provide these desirable clinical advantages. First, is an expansion catheter that includes a catheter shaft with one or more expansion elements attached to its outer surface. The expansion element(s) serve to enlarge a body lumen to reduce its elasticity and deformability when manipulated effectively fixing the relationship between the expansion catheter and a body lumen. Second, a deflection mechanism resides within the catheter shaft which, when manipulated, causes the catheter shaft to deviate from its neutral state to a curved state in which at least a portion of the catheter shaft is displaced laterally while simultaneously displacing the body lumen in contact with the expansion elements. Third, in embodiments where the expansion catheter and deflection mechanism are separate entities, the expansion catheter without a deflection mechanism is more easily introduced and positioned within a body lumen, resulting in less damage to a body lumen. Once the deflection mechanism is inserted into the expansion catheter, changing the location of the deflected portion of the expansion catheter relative to body structures is easily accomplished with the expansion elements fully expanded.

In one embodiment of the current invention which incorporates multiple balloons as expansion elements and a deflection catheter for displacement of a body lumen, when used in conjunction with a cardiac ablation procedure for treatment of atrial fibrillation, proceeds as follows: A guidewire is passed through a nasal passageway or mouth into the esophagus. An expansion catheter with its balloons in a deflated state is passed over the guidewire into the esophagus and the expansion catheter positioned at a desired location. The balloons are then inflated individually or collectively to the approximate diameter of the esophagus, fixing the catheter shaft within the esophagus. The guidewire, if used, is removed from the expansion catheter and a deflection mechanism is inserted into the central lumen of the expansion catheter and positioned therein relative to the left atrium at the desired location for repositioning of the esophagus. The deflection mechanism is then caused to curve, and the degree and plane of curvature evaluated using an imaging modality, such as fluoroscopy. In some embodiments, the location and orientation of the deflected portion of the expansion catheter is altered by moving the deflection mechanism longitudinally or rotating it circumferentially within the catheter shaft. At the completion of the procedure, the deflection mechanism is returned to its neutral position and removed from the expansion catheter. In some embodiments, the balloons are then deflated and the expansion catheter removed from the esophagus and the mouth or nasal passageway. In some embodiments of the present invention, deflection of other body lumens such as veins, arteries, urethra, fallopian tubes and various segments of the gastrointestinal tract is accomplished using the present invention.

In some embodiments, numerous benefits are derived from the use of the current invention in various clinical applications. For example, in cardiac ablations for treatment of atrial fibrillation, the esophagus can be deflected away from its natural position relative to the left atrium to reduce the probability of forming an atrial-esophageal fistula or causing periesophageal vagal plexus injury. In some embodiments, these benefits are derived from a combination of one or more of the features that are summarized as follows: First, in some embodiments, the use of multiple small balloons allows the expansion catheter to maintain its alignment within esophagus during deflection. Second, in some embodiments, the use of a plurality of small balloons provides more points of articulation along the length of the expansion catheter, which allows the catheter shaft to flex more easily to obtain the desired curvature and degree of deflection. Third, in some embodiments, because the balloons are used primarily for the purpose of maintaining alignment, the balloon pressure required during operation is lower than that needed if the balloons were also used as the primary means of deflection. This allows for balloons with thinner walls, which are inherently more flexible and have a smaller crossing profile. Fourth, in some embodiments, because the deflection mechanism is a detachable element within the expansion catheter, and the expansion catheter is inserted separately, the expansion catheter is made to be more flexible for easier entry, navigation and passage into a body lumen, especially in the presence of significant tortuosity. Fifth, in some embodiments, the lumen within the expansion catheter that houses the deflection mechanism also serves as a guidewire lumen during insertion into a body lumen, thus reducing trauma to a body lumen. Sixth, in some embodiments, movement of the deflection mechanism independent of the expansion catheter allows repositioning of the curvature relative to a body structure to be accomplished more easily while the balloons remain inflated.

BRIEF DESCRIPTION OF DRAWINGS

FIG. 2A1 is a cross-sectional view of expansion catheter 101 through plane 2A1-2A1 shown in FIG. 1B, according to some embodiments of the present invention.

FIG. 2A2 is a cross-sectional view of expansion catheter 101 through plane 2A2-2A2 shown in FIG. 1B, according to some embodiments of the present invention.

FIG. 2B is a longitudinal sectional view of expansion catheter 101 through plane 2B-2B of the expansion catheter 101 of FIG. 1B, according to some embodiments of the present invention.

FIG. 3B is a cross-sectional view at section 3B-3B of FIG. 3A, which illustrates a rectangular wire as an element of a deflection mechanism, according to some embodiments of the present invention.

FIG. 3C illustrates a deflection mechanism in a curved configuration, according to some embodiments of the present invention.

FIG. 3H is a side view of the deflection section of a deflection device 308 having an integral expansion catheter with an integral deflection mechanism contained within one lumen, according to some embodiments of the present invention.

FIG. 3i is a cross-section view of a deflection device catheter shaft 321 that includes an expansion catheter with an integral pull wire contained within one lumen, according to some embodiments of the present invention.

FIG. 6A1 is a side view of an expansion catheter 620 using a single balloon 671 wrapped in a spiral pattern around a catheter shaft, shown with balloon 671 deflated, according to some embodiments of the present invention.

FIG. 6A2 is a side view of an expansion catheter 620 using a single balloon 671 wrapped in a spiral pattern around a catheter shaft, shown with balloon 671 inflated, according to some embodiments of the present invention.

FIG. 6B1 is a partial longitudinal cross-sectional view of the expansion catheter 620 of FIG. 6A1 along section 6B1-6B1 shown in FIG. 6A1.

FIG. 6B2 is a partial longitudinal cross-sectional view of the expansion catheter 620 of FIG. 6A2 along section 6B2-6B2 shown in FIG. 6A2.

FIG. 6C is a side view of an expansion catheter 604 with a plurality of balloons 673 in which the catheter shaft 121 is located on the outside of the balloons 6730, according to some embodiments of the present invention.

FIG. 6D1 is a side view of an expansion catheter 640, with a single balloon 670 in a deflated state, in which a catheter shaft 621 passes through the center of the balloon 670 in a neutral undeflected configuration, according to some embodiments of the present invention.

FIG. 6D2 is a side view of expansion catheter 640, with single balloon 670 in an inflated state and undeflected neutral configuration, according to some embodiments of the present invention.

FIG. 6D3 is a side view of expansion catheter 640, with single balloon 670 in an inflated state, in which a catheter shaft 621 passes through the interior of the balloon 670 in a deflected configuration, according to some embodiments of the present invention.

FIG. 6D4 is a side view of an expansion catheter 650, with a single balloon 680 in a deflated state, in which a catheter shaft 623 is adhered along the side of the balloon 680 in a neutral and a deflected configuration, according to some embodiments of the present invention.

FIG. 6D5 is a side view of expansion catheter 650, in which catheter shaft 623 in its undeflected neutral configuration is adhered along the side of the balloon 680, which is in an inflated state, according to some embodiments of the present invention.

FIG. 6D6 a side view of expansion catheter 650, with single balloon 680 in an inflated state, in which catheter shaft 623 is in a deflected configuration is adhered along the side of the balloon 680, which is according to some embodiments of the present invention.

DETAILED DESCRIPTION OF FIGURES

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The embodiments shown in the figures and described here may include features that are not included in all specific embodiments. A particular embodiment may include only a subset of all of the features described, or a particular embodiment may include all of the features described.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the figures generally corresponds to the figure number in which that component is first introduced, such that the same reference number is used throughout to refer to an identical component which appears in multiple figures. Signals and connections may be referred to by the same reference number or label, and the actual meaning will be clear from its use in the context of the description.

Certain marks referenced herein may be common-law or registered trademarks of third parties affiliated or unaffiliated with the applicant or the assignee. Use of these marks is for providing an enabling disclosure by way of example and shall not be construed to limit the scope of the claimed subject matter to material associated with such marks.

Figure 1A:
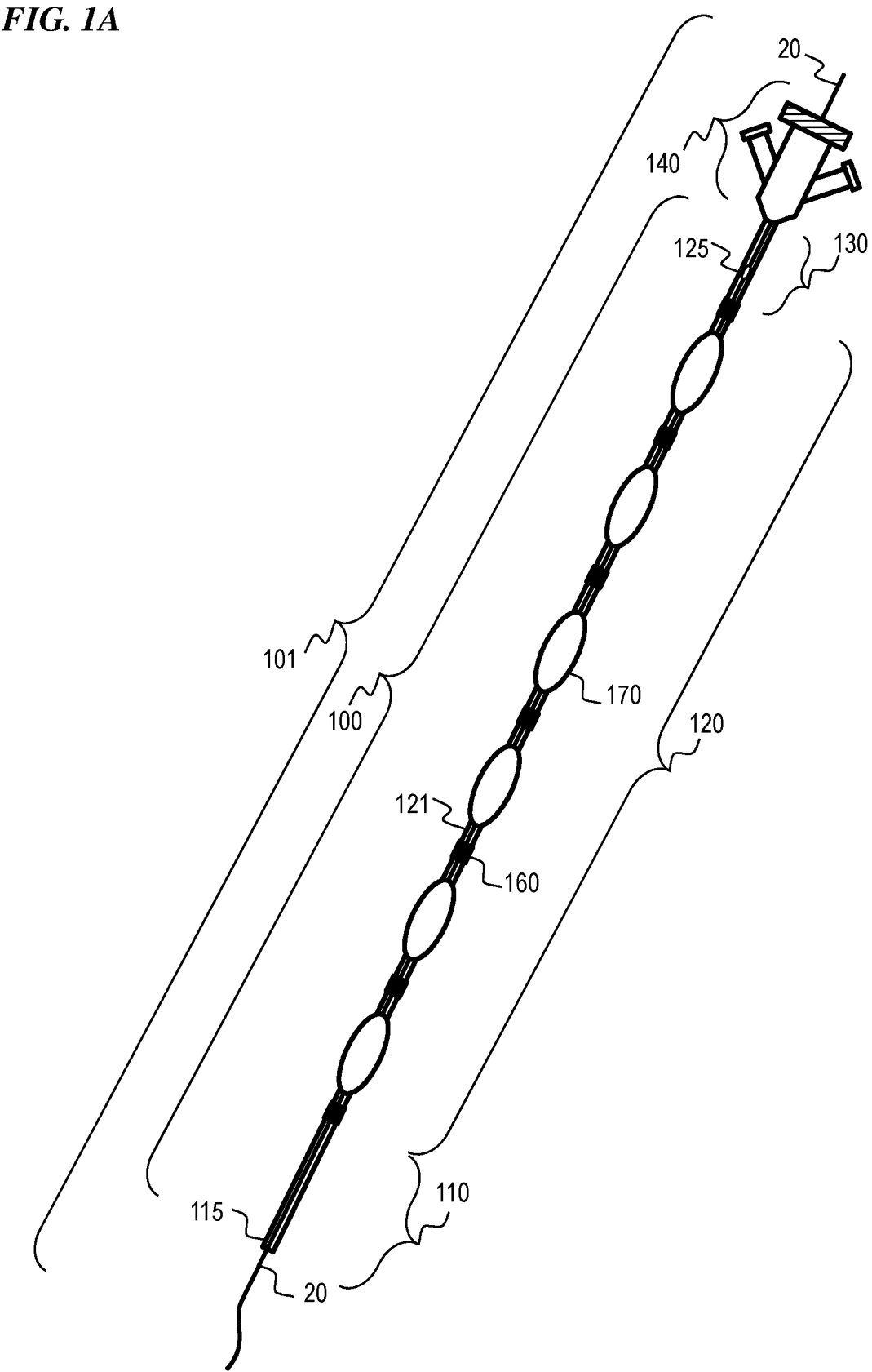
FIG. 1A is an isometric view that illustrates an expansion catheter 101 with balloons 170 deflated and a guidewire inserted and the expansion catheter in its neutral state aligned along a longitudinal axis, according to some embodiments of the present invention.

FIG. 1A is an isometric view that illustrates an expansion catheter 101 with balloons 170 deflated and a guidewire inserted and the expansion catheter in its neutral state aligned along a longitudinal axis, according to some embodiments of the present invention. FIG. 1A illustrates expansion catheter 101 in a neutral state with a guidewire inserted into its central lumen, the expansion catheter being ready for introduction into a body opening such as a nasal passageway or throat. In some embodiments, expansion catheter 101 includes two major elements: catheter body 100 and hub 140. Guidewire 20 passes through the center of hub 140 and catheter body 100 and exits at the distal tip of catheter body 100. In use, flexible guide wire 20 is fed into the intended body lumen, then the body of expansion catheter 100 is pushed into the body lumen over the guidewire to the desired position in the body lumen, then the guidewire is removed (either before or after inflating the balloons), then the deflection mechanism is inserted into central lumen 116 (see FIG. 2C) to the desired depth position, and locked at that depth by applying a desired amount of deflection and tightening a Tuohy Borst lock-and-seal mechanism 138 (see FIG. 2C) of hub 140.

Figure 1B:
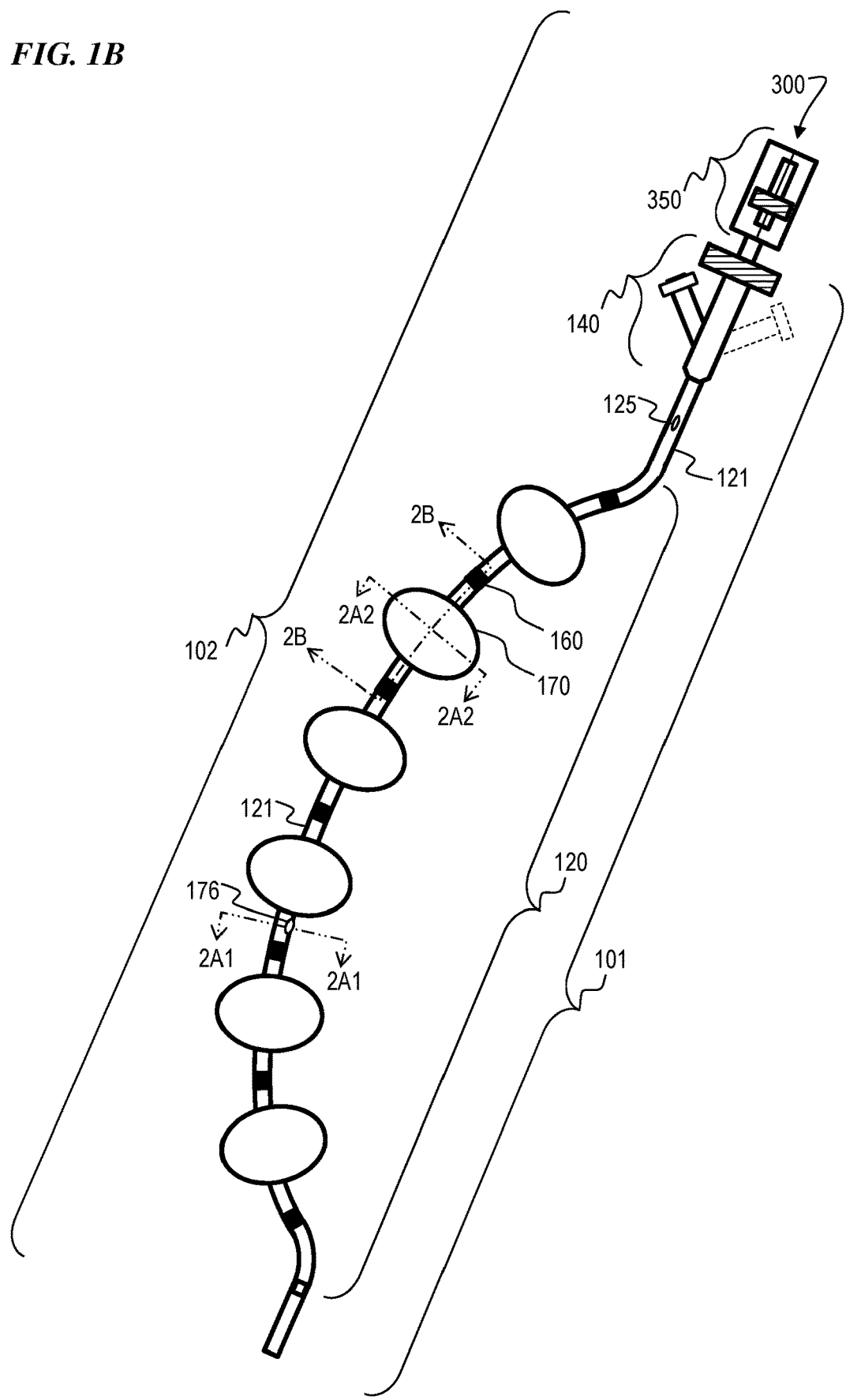
FIG. 1B is an isometric view that illustrates expansion catheter 101 with balloons 170 inflated and a deflection mechanism inserted and the expansion catheter curved relative to its longitudinal axis in a neutral state, according to some embodiments of the present invention.

FIG. 1B is an isometric view that illustrates expansion-deflection catheter 102 with balloons 170 inflated and a deflection mechanism 300 inserted and the expansion catheter curved relative to its longitudinal axis in a neutral state, according to some embodiments of the present invention. FIG. 1B illustrates expansion-deflection catheter 102 with deflection mechanism 300 inserted into expansion catheter 101 with the deflection mechanism articulated to deflect a portion of expansion catheter 101 from its normal longitudinal axis in its neutral state.

Referring to FIG. 1A, catheter body 100 includes tip section 110, articulating section 120 and proximal section 130, all operably coupled together. Hub 140 is operably coupled to catheter body 100.

Referring to FIG. 1B, articulating section 120 has at least two or more balloons 170 (six balloons 170 are shown in this embodiment of FIG. 1B) bonded to its outer catheter surface. Metal bands 160 are interspersed between the balloons 170 and also distal to the most distal balloon and proximal to the most proximal balloon 170 such that each balloon 170 is demarcated by a metal ring 160 on either side of the balloon 170 for purposes of visualization, such as by fluoroscopy. In other embodiments, the number of balloons 170 is two, three, four, or five, while in still other embodiments, the number of balloons 170 is in a range of seven to ten inclusive, a range of ten to fifteen, inclusive, or a range of sixteen to thirty, inclusive, or more than thirty balloons 170.

In some embodiments, sections 110, 120 and 130 include one or more flexible plastic tube(s) forming catheter shaft 121 made from an extrusion of a thermoplastic elastomer (and if not a single piece, then connected end-to-end), for example, made of one or more materials including but not limited to nylon, polyurethane, polyester, or polyetheretherketone. In some embodiments, the durometer of the plastic tubing 121 is in a range from 10 A to 90 D, more typically from 45 D to 72 D. In some embodiments, sections 110, 120 and 130 of catheter body 100 include a single durometer plastic or include one or more polymers of several durometers along the catheter shaft 121 to provide different responses to the action of a deflection mechanism located therein. For example, in some embodiments, it is helpful to have stiffer plastics for sections 110 and 130, which are not required to curve (or not required to curve as much), and a softer plastic for section 120, which bends in response to a deflection force. Alternatively, in some embodiments, it is beneficial to have a softer material at the distal end 110 of the catheter 101 to reduce injury or trauma to a body lumen 99 (see FIG. 4A and FIG. 4B) during insertion of an expansion catheter 101. In some embodiments, the outer diameter of catheter shaft 121 is in a range from 1 to 30 Fr (0.33 to 10.0 mm) (0.013 to 0.130 inch) inclusive, and in some such embodiments, from 4 to 9 Fr (1.33 to 3.0 mm) (0.052 to 0.118 inch). In some embodiments, the inner diameter of catheter shaft 121 (i.e., the diameter of lumen 116) is in a range from 0.1 to 10 mm (0.004 to 0.393 inch), and in some such embodiments, in a range from 0.25 to 2.5 mm (0.001 to 0.098 inch). In some embodiments, and within the scope of the current invention, that one or more diameter dimensions of the catheter shaft 121 changes longitudinally, with one or more sections among 110, 120 and 130 having different outer and/or inner diameters. In some embodiments, the plurality of balloons 170 have two or more different diameter dimensions D (see FIG. 2B) and/or length dimensions L, such that some balloons 170 have diameters D or lengths L that are different than the diameter dimensions D or length dimensions L of others of the plurality of balloons 170.

FIG. 2A1 is a cross-sectional view of catheter shaft 121 of expansion catheter 101 through plane 2A1-2A1 shown in FIG. 1B, according to some embodiments of the present invention.

FIG. 2A2 is a cross-sectional view of catheter shaft 121 and balloon 170 of expansion catheter 101 through plane 2A2-2A2 shown in FIG. 1B, according to some embodiments of the present invention. In some embodiments, catheter shaft 121 in section 120 includes an outer surface 112, inner surface 114 defining tube wall 113. In some embodiments, contained within wall 113 are one or more oblong-oval-shaped lumens 118. In some embodiments, each lumen 118 is separated from other lumens 116 and 118 and traverses the entire length of catheter body 100. At a minimum, in some embodiments, each lumen 116 and/or 118 traverses catheter body sections 120 and 130 to operably couple each lumen 116 and/or 118 to the corresponding feature in hub 140. However, some embodiments incorporate lumens 116 and/or 118 joined along part of their individual lengths, while some other embodiments terminate some lumens 116 and/or 118 along the length of the catheter body 100. In some embodiments, the lumens 116 and/or 118 serve multiple purposes, such as channels for inflation and deflation of balloons and access means for positioning instrumentation within a luminal space. In some embodiments, the lumens 116 and/or 118 can be used as conduits for injection or extraction of fluids from a surrounding luminal volumetric space, as through port 125 of FIG. 1A. In some embodiments, port 125 is operably connected to one of the lumens 118.

FIG. 2B is a longitudinal cross-section view of section 120 of expansion catheter 101 along the longitudinal centerline of expansion element 170 corresponding to sectional view 2B-2B of FIG. 1B. As shown in FIG. 2B, balloon 170 is attached to outer surface 112 of catheter shaft 121 at joint 172. As shown in FIG. 2B, the balloons 170 are bulbous shaped in their center region, from which extends a tubular section for bonding each end of the balloon 170 to a catheter shaft 121. In some embodiments, expanded balloons 170 with this profile are made from elastic or compliant materials. In some embodiments, balloons 170 have a spherical shape in their center region and a tubular section 172 at each end for attaching to catheter surface 112. Alternatively, in some embodiments, balloons 170 have a cylindrical shape in their center region and a conical section at each end from which extends a tubular section 172 for attaching to balloon catheter shaft 121. In some embodiments, balloons 170 with this shape are made from non-distensible materials. Expanded balloons are defined by a diametral dimension, D, which for a sphere or cylinder is defined as its diameter D and a length, L, defined as the shortest distance between balloon stems located on either end of the balloons for interfacing to outer surface 112 of catheter shaft 121 as illustrated in FIG. 2B. The L/D ratio for a balloon is defined as length of a balloon, L, divided by its diameter, D, when expanded to its design diameter or pressure. For some embodiments of the current invention, the L/D ratio ranges between 0.5 and 10.0, preferably between 1.0 and 5.0, and most preferably between 1.0 and 3.0.

Expansion-deflection catheter devices 102 utilizing balloons 170 with smaller L/D ratios will have better alignment of the device along the centerline of the esophagus because of the increased number of hinge points. This effectively translates more of the curvature of the device into deflection of a body lumen 99. However, smaller L/D ratios require more balloons 170, which increases design complexity and manufacturing costs.

In some embodiments, the balloons 170 are made of elastic or compliant materials which stretch when pressurized. Suitable materials include, but are not limited to, silicones of various durometers, latex rubbers of various durometers and lower-durometer polyurethanes and blends of low-durometer plastic materials such as C-Flex®. In other embodiments, balloons 170 are made of non-compliant materials that have a fixed shape and that are wrapped around a catheter shaft in their deflated state and unfold when pressurized. In some embodiments, such materials include various durometer nylons, polyethylene terephthalate (PET), polyesters and blends of different polymer families. In some embodiments, joints 172 are bonds which form a fluid seal so that the interior space of the balloon can be pressurized for purposes of expansion and deflation of the balloons. Typically, such joints are formed using an adhesive suitable for joining the materials of the balloon and catheter shaft. Examples of suitable adhesives are UV-cure adhesives such as Dymax 1161 and cyanoacrylates such as Henkel 4014. Alternatively, in some embodiments, the bond is thermally formed by reflowing both the balloon and shaft materials at a temperature and pressure sufficient to cause the materials to mix and form a homogenous material. Alternatively, in some embodiments, a mechanical bond is formed using a rigid ring to compress the balloon material against the catheter shaft material, forcing the two surfaces into intimate contact with each other, resulting in a fluid seal. In some embodiments, rings are made of, or include, one or more metals such as stainless steel, nitinol, nickel, copper, or any other ductile metal material. In some embodiments, rings are made of, or include, one or more high-strength plastics, such as nylons, polyesters, polycarbonates, or PEEK. In some embodiments, hole 174 is located on catheter shaft 121 within the interior space of balloon 170. In some embodiments, hole 174 is typically a skive, which removes the outer surface layer from a lumen 118 to operably couple the interior space of the balloon 170 to an underlying passageway of lumen 118. In some embodiments, the interior space(s) of multiple balloons are connected to a single lumen 118, each via an internal skive hole 174, whereby all balloons are inflated at one time, while in other embodiments, each balloon 170 is connected to its own dedicated lumen 118, allowing separate individual balloon inflations/deflations. Some embodiments use a combination of the two approaches, wherein one or more balloons 170 are coupled to each one of a plurality of lumens 118.

FIG. 1B shows marker bands 160 placed along catheter body section 120 to demarcate each balloon for purposes of visualization (e.g., when imaged using x-ray or fluoroscopy). In some embodiments, marker bands 160 are made of a radiopaque material to be visible under fluoroscopy. In some embodiments, bands are made of (or include) metal such as stainless steel, Nitinol, nickel, copper, or any other ductile metal. In some embodiments, rings 160 are adhesively bonded to the outer surface 112 of the catheter shaft at joint 162 as shown in FIG. 2B. In some embodiments, the rings are mechanically crimped onto outer surface 112 to form an interference fit. In some embodiments, rings used for marker bands 160 are placed over each balloon stem 172 to enhance the seal of a balloon 170 to the catheter shaft 121 outer surface 112, thus allowing marker bands 160 to serve two functions: both as visualization indicia and as balloon seals.

In some embodiments, one or more skive holes 174 are formed in the surface 112 of a catheter shaft and located in any suitable catheter position along catheter body 100. In some embodiments, one or more skive holes 176 is/are operably coupled to the exterior environment inside the body lumen and outside or surrounding the balloons 170, and to one or more lumens 118 contained within catheter shaft 121. In some embodiments, one or more skive hole(s) 176 serves as a port through which fluids are injected into or extracted from the luminal volume between two balloons and the interior surface of a body lumen. In some embodiments, each skive hole 176 and its operably coupled lumen 118 also functions as a conduit through which instrumentation, such as temperature probes, are inserted into the luminal space between the balloons and the interior surface of a body lumen.

Figure 2C:
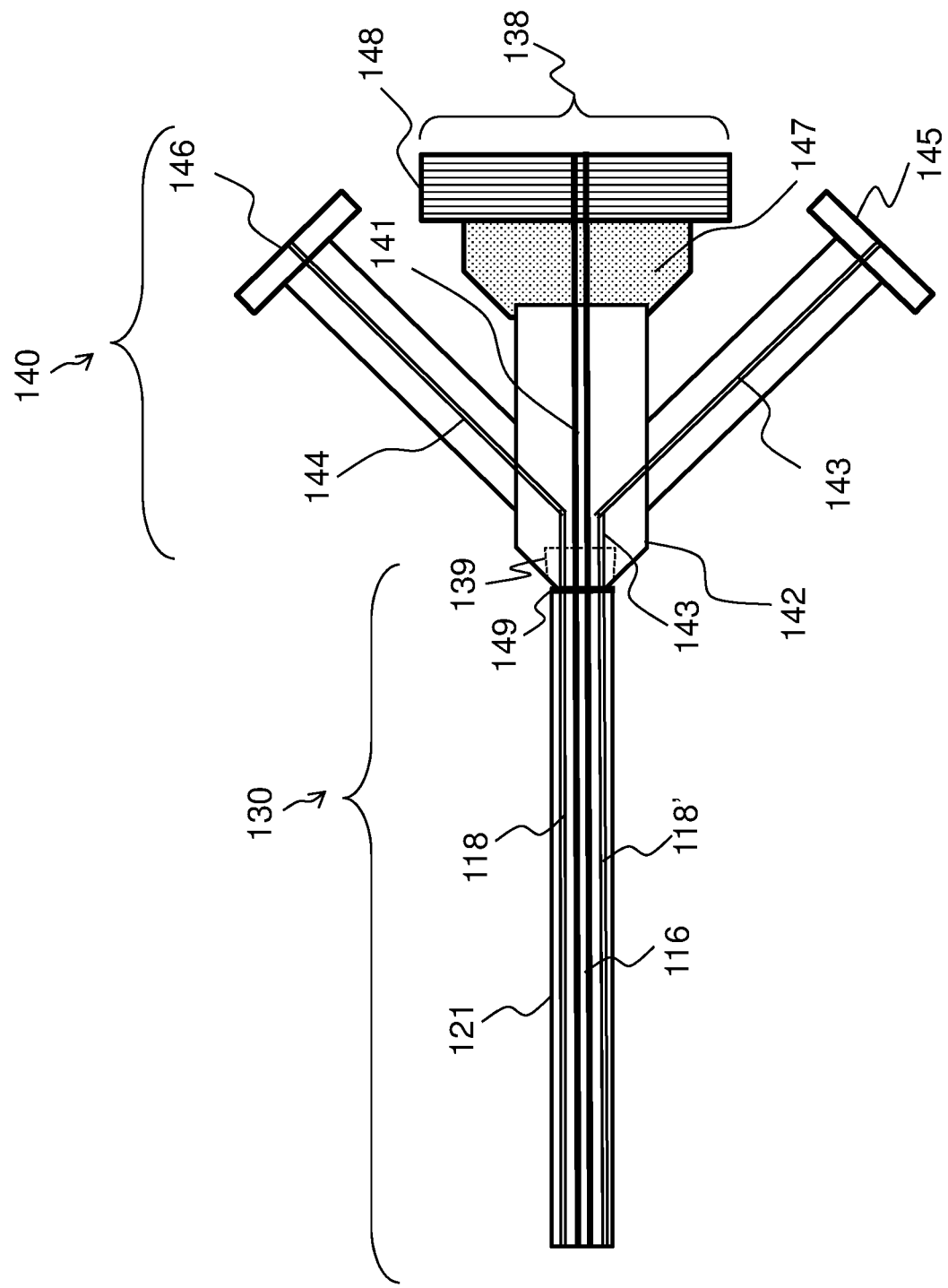
FIG. 2C is a cross-sectional view hub 140 of an expansion catheter 101, according to some embodiments of the present invention.

FIG. 2C illustrates one embodiment of hub 140 of FIG. 1A. At the center of hub 140 is elongated plastic member 142 to which are operably coupled one or more side arms 145 and/or 146. In some embodiments, side arms 145 and/or 146 terminate in a luer fitting for connecting to a mating fitting, such as that of a syringe. Contained within sidearm 145 is internal lumen 143 and contained within sidearm 146 is internal lumen 144. Both lumens 143 and 144 extend into and through the interior of hub 142 which also contains central lumen 141. In some embodiments, the distal end of hub 140 contains a recessed well 139 into which catheter section 130 is inserted and adhesively bonded to form fluid seal 149. Lumens 143 and 144 are in fluid communication with one or more respective lumens 118 and/or 118' of catheter shaft 121. In some embodiments, attached at the proximal end of plastic member 142 is a Tuohy Borst assembly 138 that includes cap 148 and gasket 147. The hole in the cap 148 of the Tuohy Borst assembly 138 is in fluid communication with central lumen 141 of hub 140 which in turn is in fluid communication with central lumen 116 of catheter shaft 121. In some embodiments, sidearms 145 and 146 serve one or more of several functions. In some embodiments, one of the side arms is used for inflation and deflation of the balloons attached to catheter body 100. In some embodiments, one of the side arms 145 and 146 is used to inject and extract fluids from the luminal volumetric space contained between the delivery catheter and the inner wall of a body lumen such as through port 125 of FIG. 1A. In some embodiments, the lumen 141 through the Tuohy Borst assembly 138 of hub 140 is used for housing a guidewire 20 during insertion of an expansion catheter 101 into a body lumen, or for housing a deflection mechanism 300 for changing the shape of an expansion-deflection catheter device 102.

FIG. 1A illustrates the use of a multiple balloons 170 individually affixed to a catheter shaft 121, each as shown in the cross-sectional view of FIG. 2B, to effectively center a catheter shaft 121 in a body lumen in a straight state as shown in FIG. 1A, or in a curved state as shown in FIG. 1B.

Figure 2D:
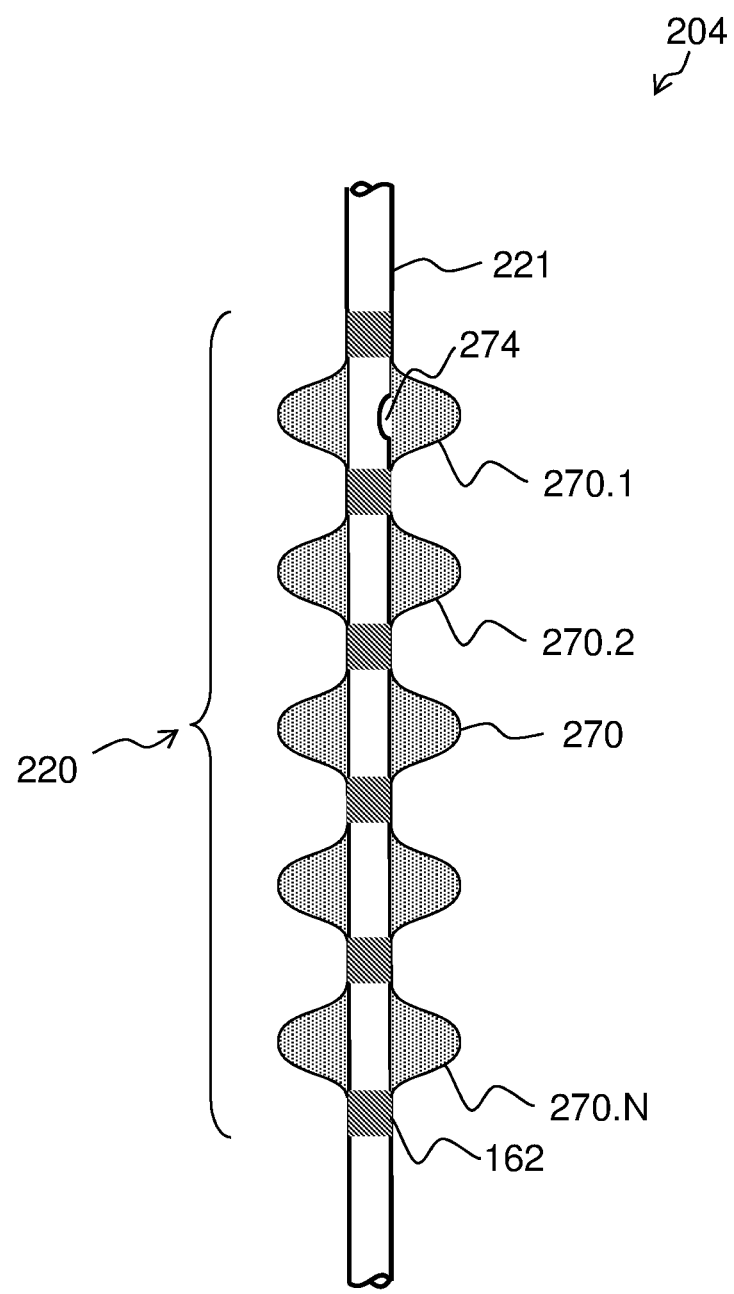
FIG. 2D is a side view of a central portion 220 of an expansion catheter 204 that uses a single balloon 270 that is mechanically segmented to form a plurality of expanded bulbous portions 270.1, 270.2, . . . 270.N along a catheter 221, according to some embodiments of the present invention.

As illustrated in FIG. 2D, the same effect can be achieved with a single balloon that has multiple segments incorporated into the overall balloon shape. In some embodiments, for a balloon 270 that includes a compliant or semi-compliant material, marker bands 162 are used, not only as indicia for x-ray positioning of the device, but also to affix the balloon 270 as multiple inflatable segments to the catheter shaft 221, effectively creating multiple sealed spaces from one larger space. In some embodiments, for a balloon 270 that includes semi-compliant or non-compliant materials, the segmented geometry is fabricated into the balloon 270 during balloon formation, with the balloon stems bonded to the shaft at the two ends and/or at each intermediate location with a thermal (fusing the balloon material to catheter shaft 221 using heat), adhesive (using a compatible adhesive) and/or mechanical (using marker bands 162) bond.

Figure 3A:
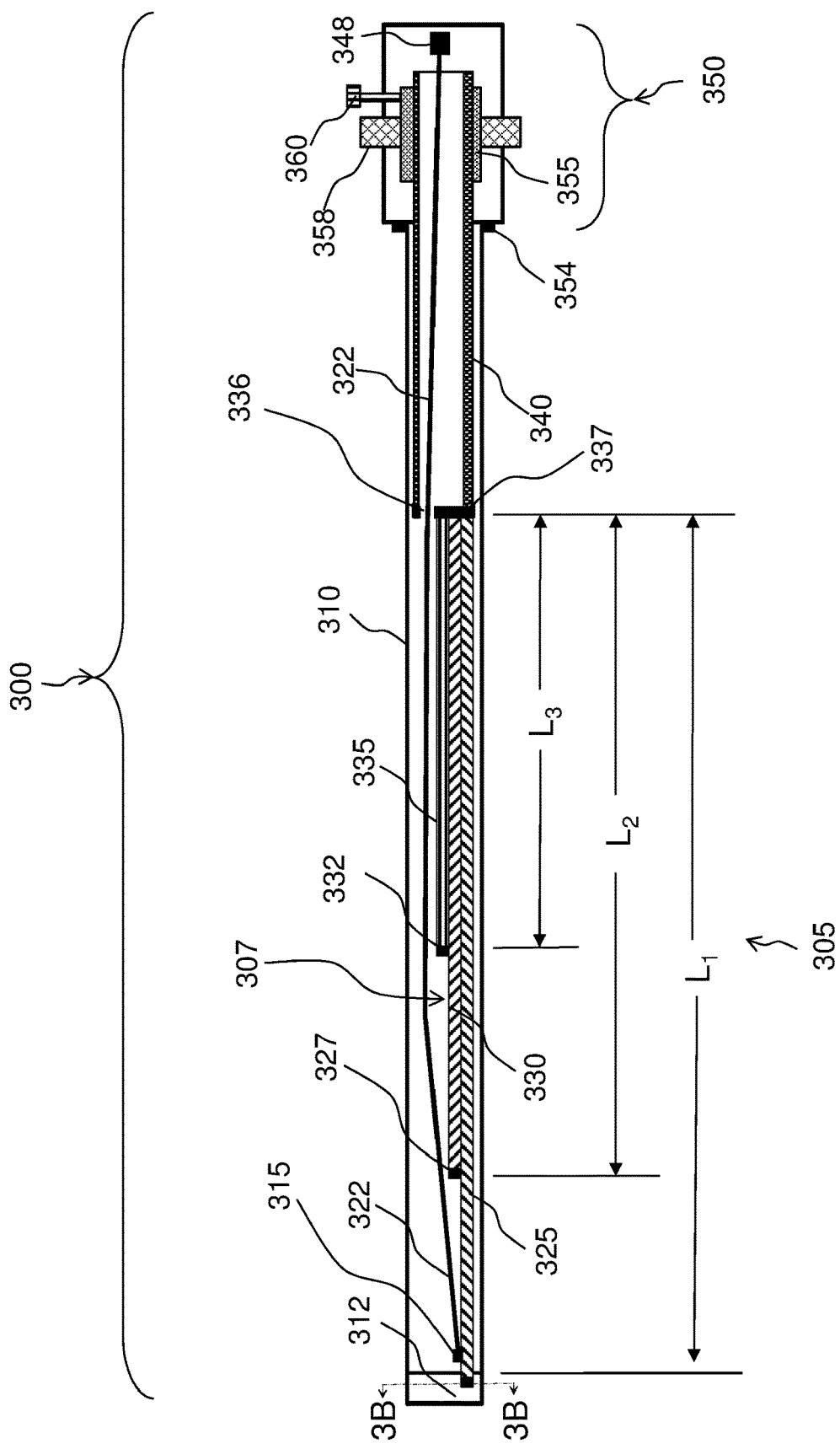
FIG. 3A is a longitudinal cross-sectional view of a deflection mechanism 300 for insertion into an expansion catheter, according to some embodiments of the present invention.

FIG. 3A shows a longitudinal cross sectional view of deflection mechanism 300. In some embodiments, deflection mechanism 300 includes four important elements, namely:
(1) flexible section 305 which contains a number of longitudinal elements which deflect in response to action of a tensioning wire;
(2) tensioning wire 322 which moves longitudinally within column 340;
(3) column 340 which reacts to forces generated by a tensioning wire; and
(4) handle 350 which contains a knob which interfaces with column 340.

Referring to FIG. 3A, the outer shell of deflection mechanism 300 includes outer tube 310 to which is affixed tip 312 at its distal end and handle assembly 350 at its proximal end. In some embodiments, the distal section of deflection mechanism 300 is flexible and curves, while the proximal section is more rigid and remains relatively straight. In some embodiments, the flexible section 305 contains leaf-spring assembly 307. In some embodiments, the rigid section contains column 340 and tensioning wire 322.

In some embodiments, outer tube 310 is bonded to tip 312 on its distal end and to handle 350 on its proximal end. Outer tube 310 provides a container for the internal contents of deflection mechanism 300 and contains a lubricious outer surface to aid in the insertion and positioning within expansion catheter 101 of FIG. 1A. In one preferred embodiment, outer tube 310 is made of a lubricious material such as the Teflon® family, PTFE (polytetrafluoroethylene), ETFE (ethylene tetrafluoroethylene), or PFA (perfluoroalkoxy alkane) or from the polyethylene family, HDPE (high-density polyethylene) or LDPE (low-density polyethylene). Alternatively, a less lubricious material such as a nylon, polyester or polyurethane is used in some embodiments, and a lubricious coating applied to its outer surface using commonly available deposition methods well known to one schooled in the art, such as Applied Membrane Technology's Silglide™ coating. Outer tube 310 is bonded to distal tip 312 and handle 350 using compatible adhesives for the materials being joined.

In some embodiments, leaf-spring assembly 307, contained within the central lumen of outer tube 310, includes rectangular wires 325, 330 and 335 which form a composite structure which bends in a single plane when a longitudinal force is applied to its distal end and returns to its neutral position upon release of the force. Rectangular wire 325 has a longitudinal length $L_1$ measured from its most proximal edge located at junction 337 to the most proximal edge of tip 312. In some embodiments, rectangular wire 330 begins at the same proximal location 337 and extends distally along wire 325 to 327, a length $L_2$ where $L_2$ is less than $L_1$. In some embodiments, rectangular wire 335 is similarly configured to begin at the same proximal location and extend distally to joint 332—a length $L_3$ where $L_3$ is less than $L_2$. In some embodiments, wires 325, 330 and 335 are made of high-strength metals such as tempered stainless steel, Nitinol, and/or hardened steels or high-durometer plastics such as PEEK, nylon 6/6, polyimides, or liquid crystal polymers (LCP).

Rectangular wires are defined by a width W and a height H as shown in FIG. 3B. For some embodiments of the current invention, W is in a range from 0.25 to 10 mm (0.001 to 0.39 inch) inclusive, and in some such embodiments, W is in a range from 0.5 to 5 mm (0.020 to 0.197 inch) inclusive, or from 1.0 to 2.5 mm (0.039 to 0.098 inch) inclusive. For some embodiments of the current invention, H is in a range from 0.125 to 5 mm (0.005 to 0.197 inch) inclusive, and in some such embodiments, H is in a range from 0.25 to 2.5 mm (0.001 to .098 inch) inclusive, or from 0.5 to 1.25 mm (0.020 to 0.049 inch) inclusive. For some embodiments of the current invention, $L_1$ is in a range from 11.0 to 18.0 cm (4.33 to 7.08 inch) inclusive, and in some such embodiments, in a range from 14.0 to 16.0 cm (5.51 to 6.29 inch) inclusive. For some embodiments of the current invention, $L_2$ is in a range from 6.0 to 11.0 cm (2.36 to 4.33 inch) inclusive, and in some such embodiments, in a range from 7.0 to 10.0 cm (2.76 to 3.94 inch). For the current invention, $L_3$ can range from 3.0 to 9.0 cm (1.18 to 3.54 inch) but preferably from 4.0 to 6.0 cm (1.57 to 2.36 inch).

In some embodiments, attached to the distal end of leaf-spring assembly 307 is tensioning wire 322 which is affixed to rectangular wire 325 at joint 315. in some embodiments, the proximal end of tensioning wire 322 is affixed to handle 350 at joint 348. In some embodiments, tensioning wire 322 includes a high-strength metal such as tempered stainless steel, Nitinol, and/or other hardened steels. For some embodiments of the current invention, wire diameters range from 0.05 to 1.0 mm (0.002 to 0.040 inch) inclusive, preferably from 0.1 to 0.5 mm (0.004 to 0.020 inch) inclusive, more preferably around 0.3 mm (0.012 inch) inclusive. In some embodiments, joint 315 includes silver solder or an adhesive.

In some embodiments, attached to the proximal end of leaf-spring assembly 307 is adapter 337 which anchors the proximal end of flat wires 325, 330 and 335 and also has a through hole 336 for passage of tensioning wire 322. In some embodiments, each flat wire is soldered or adhesively bonded into a well on the distal side of adapter 337.

In some embodiments, attached to the proximal side of adapter 337 is column 340. In some embodiments, column 340 includes a thin-walled metal tube, such as a hypodermic tube. In some embodiments, the hypodermic tube is made of high-strength metals such as hardened stainless steel, Nitinol, and/or other hardened steel alloys, or high-durometer plastics such as PEEK, nylon 6/6, polyimides, or liquid crystal polymers (LCP). In some embodiments, the outer diameter of hypodermic tube 340 is in a range from 0.5 to 5.0 mm (0.020 to 0.198 inch) inclusive, more preferably from 1.0 to 2.5 mm (0.039 to 0.098 inch) inclusive. In another embodiment of the current invention, column 340 includes a tightly wound wire coiled tube like the outer casing of a speedometer cable. In some embodiments, the wire composition includes high-strength metals such as tempered stainless steel, Nitinol, and/or hardened steel alloys. In some embodiments, wire diameter is in a range from 0.05 to 1.0 mm (0.002 to 0.039 inch) inclusive. In some embodiments, the outer diameter of the wire coil structure is in a range from 0.5 to 5.0 mm (0.020 to 0.198 inch) inclusive, more preferably from 1.0 to 2.0 mm (0.039 to 0.078 inch) inclusive.

In some embodiments, the proximal end of column 340 is bonded to slide assembly 355. In some embodiments, slide assembly 355 includes a metal tube with external threads which mate with corresponding internal threads contained within knob 358. In some embodiments, tensioning wire 322 passes through the hole in adapter 337, through the center of column 340, through slide 355, terminating in the proximal region of handle 350 at joint 348. In some embodiments, locking device 360 is a threaded assembly used to fix the position of knob 358 during operation to prevent unintended changes in the curvature of deflection mechanism 300 during use.

The function of deflection mechanism 300 is to laterally displace a portion of the straight line defined by connecting tip 312 and handle 350 when the deflection mechanism in its neutral state, i.e., with no force on tensioning wire 322, as shown in FIG. 3A.

In some embodiments, as force is applied to tensioning wire 322, an arc is created in spring assembly 307 defined by an axial length $L_x$ and a lateral displacement $D_y$ as shown in FIG. 3C. This displacement results from tensioning wire 322 causing the distance between the distal and proximal ends of rectangular wire 325 to foreshorten by virtue of moving a portion of rectangular wire 325 laterally, i.e., perpendicular to its longitudinal axis in its neutral state. There are several important design considerations to accomplish the requisite lateral displacement for a given application. First, in general, the axial length of the displaced section $L_x$ is controlled by the distance between the location of joints 315 and 337 of FIG. 3A. As this distance increases, the length of the curved section correspondingly increases. For the current invention, curves can range up to 20.0 cm (7.87 inch), preferably up to 12.0 cm (4.72 inch), and more preferably from 3.0 to 5.0 cm (1.18 to 1.97). Second, the lateral displacement $D_y$ is controlled by longitudinal movement or stroke length of knob 358. Longer stroke lengths result in more lateral deflection. For the current invention, lateral displacements can range up to 10.0 cm (3.93 inch), preferably up to 6.0 cm (2.36 inch), and more preferably from 1.5 to 4.0 cm (0.59 to 1.57 inch). Third, there is an interrelationship between $L_x$ and $D_y$: As $L_x$ becomes longer, the stroke length to achieve an equivalent $D_y$ also becomes longer. Because stroke length is implemented in the handle, there is a finite stroke length beyond which the handle length would be clinically impractical. For the current invention, stroke lengths can range up to less than 5.0 cm (1.96 inch), preferably up to less than to 3.0 cm (1.18 inch). Fourth, the force required to move the deflection mechanism into a curve configuration depends on the thickness of the wires used in the deflection mechanism. Using beam-bending analysis, deflection forces increase as the cube of wire thickness, H, and linearly with wire width, W. The benefit of thicker wire is the curvature will be more repeatable and the deflection mechanism can withstand more force before buckling or bending sideways. This is particularly important when the forces required to deflect the body lumen are large. Fifth, the geometry of the arc depends on the relationship between the rectangular wires used in the deflection mechanism: As the distance $L_1$, $L_2$ and $L_3$ decrease, the radius of curvature will become smaller. If the distances $L_1$-$L_2$ and $L_2$-$L_3$ are equal, the curve will be more uniform and approximate part of a circular arc. Unequal segment lengths will change the curvature, causing a portion of the arc to have a larger radius of curvature and other portions to have a smaller radius. Such shapes may be advantageous to provide non-circular arcs for the purpose of navigating tortuous pathways or deflecting around multiple body structures.

FIG. 3A is a longitudinal cross-sectional view of a deflection mechanism 300 for insertion into an expansion catheter, according to some embodiments of the present invention. FIG. 3A shows an embodiment of the deflection mechanism of the current invention using three wires, each wire having a similar cross section defined by its width, W, and height, H and lengths $L_1$, $L_2$ and $L_3$. Other embodiments are possible within the scope of the current invention to accomplish the same mechanical deflection as the illustrated device. One such example is the use of more wires of similar cross section each having a different length. Assemblies containing 2, 3, 4, 5, 6 or up to 20 wires fall within the scope of the present invention. In some embodiments, individual wires with different widths W and heights H are combined within one leaf spring assembly. Because the use of more wires comes with attendant increase in manufacturing difficulty, in some embodiments of the current invention a single wire with a larger height H is used with a longitudinal cross-sectional profile which changes between the equivalent points defined by $L_1$ and $L_3$. In some embodiments, such a shape is mechanically ground or chemically etched into its height profile within the distal region corresponding to the section defined by $L_1$ thru $L_3$. In some embodiments of the current invention a single wire with width W is used with a longitudinal cross-sectional profile which changes between the equivalent points defined by $L_1$ and $L_3$. The longitudinal profiles may be such that they vary continuously along the longitudinal length or may have multiple discrete changes in which a given section has a uniform profile for a defined distance less than the total distance between $L_1$ to $L_3$. In some embodiments of the current invention a combination of wires with a uniform cross sectional longitudinal profile is combined with ones with a variable longitudinal profile. In some embodiments, such inner assembly designs are used to change the shape of the arc used to deflect the catheter to obtain the desired deflection curvature.

The deflection mechanism of FIG. 3A shows a device in which lateral displacement occurs within a single arc in one plane. In some embodiments of the current invention, a deflection mechanism based on the same principles of operation is designed such that displacement occurs in different geometric arc configurations and occurs in multiple planes. For example, in some embodiments of the current invention a deflection mechanism has two different radii of curvature but still occurs within the same plane. Such a design involves adding a second tensioning wire with a contact point proximate to 315 with the tensioning wire interfacing with a second knob on handle 350 similar to that of tensioning wire 322 with knob 358. Another embodiment includes a deflection mechanism in which the lateral deflection occurs in two different planes. Such a design is possible by making one or more wires 325, 335 and 340 more square, W/H ratio closer to 1 and adding a second tensioning wire with a joint on a wire face 90 degrees to the face of the wire that contains joint 315, and interfacing this second tensioning wire with a second knob on handle 350 similar to that of tensioning wire 322 with knob 358.

In one embodiment of the current invention, deflection mechanism 300 and expansion catheter 101 of FIG. 1A are separate entities which are operably combined by inserting deflection mechanism 300 into a lumen of expansion catheter 5. Expansion catheter 101 is designed such that lateral displacement of deflection mechanism 300 results in a corresponding lateral displacement of at least a portion of catheter body 100 of expansion catheter 101. The location of the deflection section and rotation of the deflected section relative to the Tuohy Borst hub 140 can be changed by slideably moving and/or rotating deflection mechanism 300 within expansion catheter 101.

In another embodiment of the current invention, a passive stylet is used to shape the deflection device 10. In such embodiments using passive stylets, the curved stylet is used similarly to deflection mechanism 300 to curve a section of expansion catheter 5.

Figure 3D:
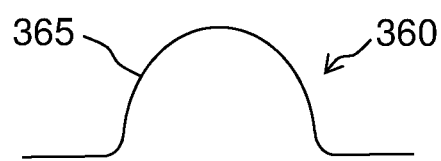
FIGS. 3D and 3E illustrate passive stylets each with a single plane of curvature, according to some embodiments of the present invention.

FIG. 3D shows the distal end of stylet 360 made of wire 365 shaped with a single deflection curve for insertion into deflection catheter 101. The wire can be made from stainless steel, Nitinol, or any high-strength metal which when shaped can provide the requisite force to deflect a body organ. In various embodiments of the present invention, wire sizes range from 0.1 to 2.0 mm (0.004 to 0.079 inch).

Figure 3E:
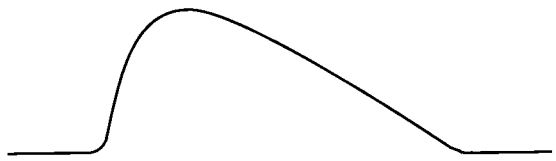
Figure 3F:
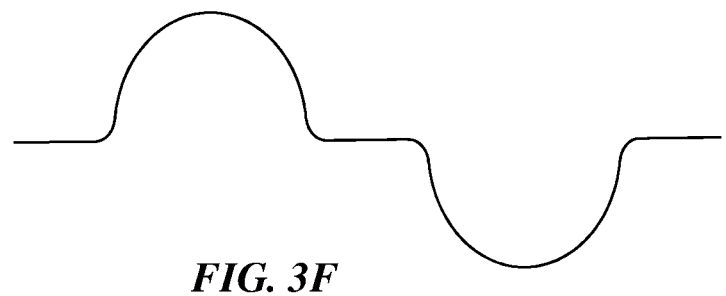
FIG. 3F illustrates a passive stylet with two curves in a single plane of curvature, according to some embodiments of the present invention.
Figure 3G:
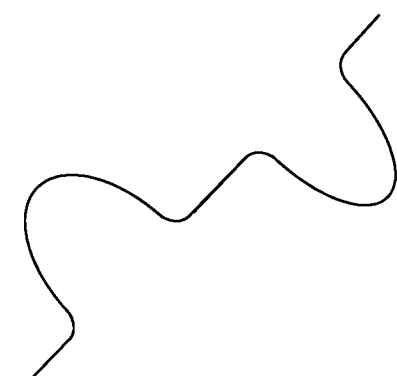
FIG. 3G illustrates a passive stylet with two curves in two different planes of curvature, according to some embodiments of the present invention.

FIG. 3E illustrates a geometry which is not a segment of a circular arc. FIG. 3F illustrates a geometry which contains a compound curvature that lies in a single plane. FIG. 3G illustrates a geometry in which the compound curvature lies in two different planes.

In another embodiment of the current invention, junction 315 is laterally displaced from tip 312 to provide a section distal to junction 315 which is not deflected. This may be advantageous in certain applications to provide a more uniform transition between the end of the deflected section of an expansion catheter and its distal non-deflected section. The greater the distance between junction 315 and tip 312, the longer the transition region.

In another embodiment of the current invention, deflection mechanism 300 and balloon center catheter body 100 are designed as a single combined integral unit forming expansion-deflection catheter device 308. One main advantage of this design is fewer parts/materials, with a corresponding reduction in overall device diameter. The location of the deflected section and rotation of the deflected section relative to the Tuohy Borst hub 140 of expansion catheter 101 is fixed and not changeable during use.

One embodiment of an integral unit of the current invention is shown in FIG. 3H, in which the deflection mechanism is integral to the expansion catheter. In this embodiment, tension wire 322 passes through lumen 118 of catheter body 112 and is anchored at the distal end of the deflection zone 120 of expansion catheter 101 at junction 392. In some embodiments, metal support ring 390 is used to reinforce the junction 390 to distribute the forces in tension wire 322 over a larger surface area. At the proximal end of deflection zone 320, support 337 is bonded to catheter shaft 112 and column 340 to provide the pivot point for proximal defection of the expansion catheter. Balloons 170 and rings 160 are attached to catheter shaft 112 as previously described.

In operation for a preferred embodiment of the current invent using separate expansion and deflection elements, expansion catheter 101 is prepared for insertion into a body cavity by flushing its central lumen with a biocompatible fluid such as physiological saline. A guidewire, preferably one with a diameter of 0.089 mm (0.035 inch), is inserted into a body orifice and then into the intervening body passageways so that the distal tip of the guidewire is placed distal to the region where expansion catheter 101 will reside in a body lumen. For example, for esophageal deflection, the tip of the guidewire is positioned near the entrance to the stomach, i.e., above the pyloric sphincter. If used in a procedure, the guidewire is then back-loaded through catheter tip 115, through lumen 116 exiting at the proximal end through Tuohy Borst cap 148. Use of a guidewire is typically more important for narrow and tortuous passageways such as those through the nasal cavity when used for the purpose of esophageal deflection. Expansion catheter 101 is then inserted into a body orifice and threaded through the intervening passageway until it is positioned at the desired location. For example, in an esophageal application, the tip of the expansion catheter 115 is inserted through the mouth and into the throat and then into the esophagus. The tip is then positioned near the lower part of the esophagus in a region above the pyloric sphincter. In some embodiments, the position of the catheter is evaluated using fluoroscopy and rings 160 positioned on expansion catheter 5. In some embodiments, to further enhance imaging a fluid media such as a radiopaque salt diluted with physiological saline is injected through one of the hub ports to inflate balloons 170. At minimum, once expansion catheter 101 is positioned, each balloon is inflated via an inflation port on the hub such that the outside surface of the balloon is in contact with the interior walls of a body lumen, which effectively fixes the position of the expansion catheter 101 within the body lumen along its centerline. In some embodiments, the degree of balloon Inflation and positioning is rechecked using fluoroscopy. The guidewire is then removed from expansion catheter 101 and deflection mechanism 300 inserted into expansion catheter 101 via Tuohy Borst 148 traversing central lumen 116 of catheter body 100 forming deflection device 10. Deflection mechanism 300 is positioned within balloon deflection device 102 so that the section of the deflection mechanism which curves is aligned with section 120 of the expansion catheter body 100. Once proper alignment is obtained, the position of the deflection mechanism is fixed by tightening cap 148 on the Tuohy Borst assembly 138 of hub 140. In some embodiments, deflection of the catheter is accomplished by rotating knob 358 of handle 350 until the desired lateral displacement of deflection device 102 is attained, at which point the position of knob 358 can be locked using screw 360. In some embodiments, confirmation of the location, degree and plane of deflection relative to critical anatomical structures is assessed using fluoroscopy. For example, in the use of the current invention for esophageal deflection, the position of the esophagus relative the left atrium is evaluated. The location, degree and plane of deflection can be changed by adjusting the position of deflection mechanism 300 relative to deflection device 102. At the completion of a procedure, the deflection mechanism is returned to its neutral position and then removed from the deflection device. All balloons 170 are deflated and the expansion catheter 101 removed from the body lumen 99.

Figure 4A:
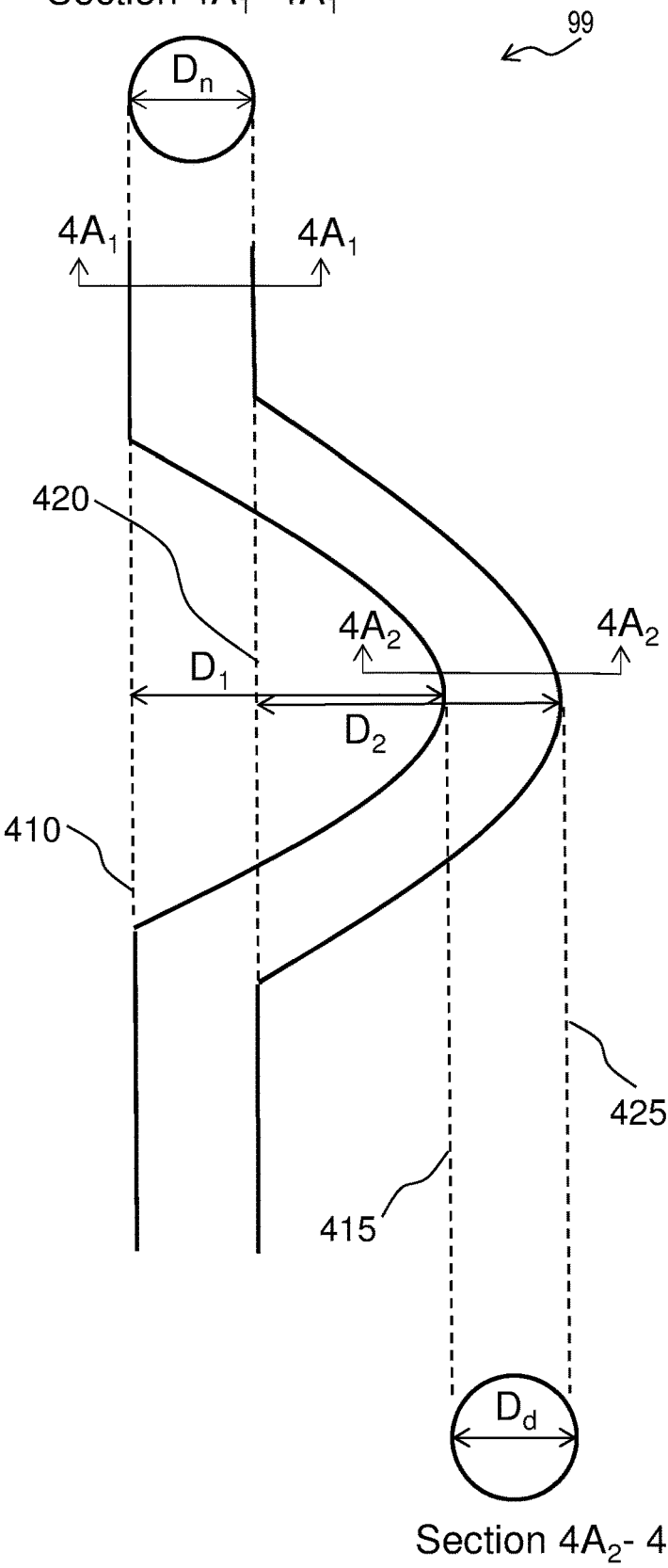
FIG. 4A is a side-view cross-section view of a body lumen 99 that illustrates lateral displacement of the body lumen 99 without deformation of the body lumen 99, according to some embodiments of the present invention.

One major benefit of using the current invention is the ability to maintain the circularity of a body lumen in the region of deflection. The ability of a device to maintain circularity can be evaluated by defining a cross-sectional profile of a body lumen in a region away from the deflected section to that of a cross-sectional profile in the region of deflection and comparing the two profiles. Referencing FIG. 4A, this would correspond to sectional views 4A1-4A1 and 4A2-4A2, respectively. For each cross-sectional profile, the largest distance, D, between any two diametrically opposite interior surfaces is measured. Referring to FIG. 4A, the values would be $D_n$ for a cross-sectional profile away from the deflected region and $D_d$ for the cross section in the deflected region. The values for these two measurements are then compared. For devices which maintain circularity of a deflected lumen, these two values will be nearly identical.

Figure 4B:
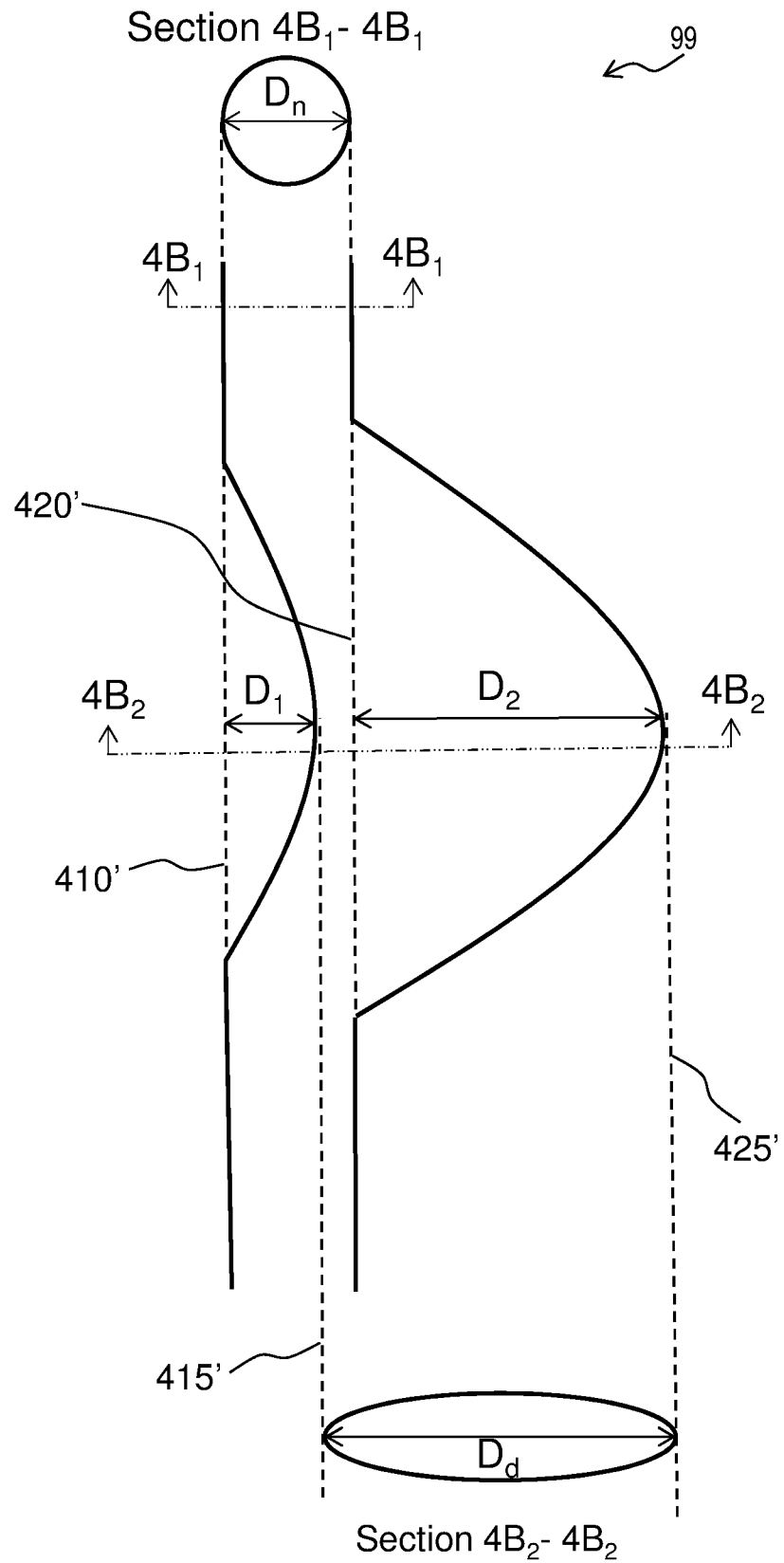
FIG. 4B is a side-view cross-section view of a body lumen 99 that illustrates both lateral displacement and deformation of the body lumen 99, according to some embodiments of the present invention.

FIG. 4A illustrates a body lumen which has been moved laterally using a deflection device of the current invention which maintains the circularity of the body lumen. On the other hand, FIG. 4B illustrates lateral movement using a deflection device that includes a flexible tube with an integral deflection device in which the outer diameter of the device is smaller than that of the body lumen into which it is inserted. In FIG. 4A, because deflection is accomplished using the current invention, the circularity of the body lumen is approximately preserved during deflection, as indicated by comparable values for $D_n$ and $D_d$. However, referring to FIG. 4B, because there is significant initial stretching of the body lumen during deflection, the profile is more elliptical in the deflected region, resulting in $D_d$ being much larger than $D_n$.

Another measure of the benefit of using the current invention is to calculate the translational efficacy of a deflection device. This parameter characterizes the ability to translate lateral displacement of a device into corresponding movement of a body lumen. This analysis measures the deflection of diametrically opposite points of a cross section of a body lumen from its original or non-deflected position. A reference line for the original position of a body lumen is defined by drawing a line connecting the outside edge of the body lumen above and below the deflected section. This is done for two diametrically opposite points on the body lumen. Referring to FIG. 4A, this defines lines 410 for one edge and line 420 for the diametrically opposite edge. For FIG. 4B, the corresponding designations are 410' and 420'. Using these two defined reference lines, the maximum deflected distance for each edge of the body lumen is measured from its corresponding reference line as the perpendicular distance from the reference line to the point of maximum deflection for the same point on the body lumen. For FIG. 4A, this corresponds to distances $D_1$ and $D_2$ and for FIG. 4B, distances $D_1'$ and $D_2'$. Using this nomenclature, a translational efficacy can be defined as $\{1-(D_2-D_1)/[(D_2+D_1)/2]\}$ for FIG. 4A and $\{1-(D_2'-D_1')/[(D_2'+D_1')/2]\}$ for FIG. 4B. For a translation efficacy of 1.0, all motion of the device would be transferred into a corresponding movement of the centerline of the body lumen.

Referring to FIG. 4A, for a deflected section in which the cross section of the body lumen is not deformed, $D_1$ and $D_2$ are nearly equal and the translational efficacy is close to 1.0. However, for FIG. 4B, where there is significant deformation of the cross section of the body lumen in the deflected section, $D_2$ is much larger than $D_1$ yielding a translational efficacy that approaches zero or, in the worst case, even less than zero. For the current invention, the translational efficacy is preferably greater than 0.5, more preferably greater than 0.75, and most preferably greater than 0.85.

Some embodiments of the current invention use other expansion means for locating expansion catheter 101 within a body lumen. In some embodiments, other means include but are not limited to nitinol wires in the form of a spline or a braided mesh in the form of a sphere. Such means would be activated from a collapsed state with a diameter approximately that of expansion catheter 101 to that of a body lumen by moving the two ends of each entity towards each other either by tensioning or pushing one end. It is also envisioned within the scope of the current invention that balloons and expandable wire means could be used in combination with each other to form the expansion means for expansion catheter 101.

Figure 5A:
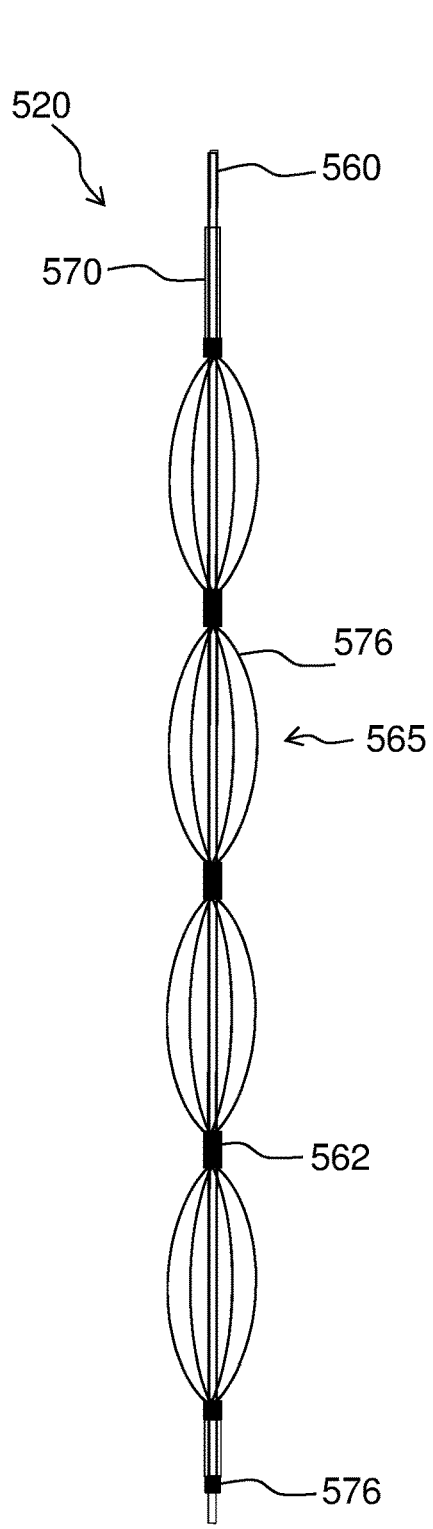
FIG. 5A is a side view of a deflection device 520 using a pre-shaped wire spline as an expandable element, according to some embodiments of the present invention.

FIG. 5A is a side view of a deflection device 520 using a pre-shaped wire spline as an expandable element, according to some embodiments of the present invention. FIG. 5A illustrates deflection device 520 that uses a wire spline as an expandable element. In this embodiment, multiple formed wires 576 are attached to metal rings 562 on each end to form spline assembly 565. Multiple spline assemblies are linked together by attaching the distal end of one spline assembly to the proximal end of the next spline assembly via ring 562. The most proximal spline assembly has tube 570 as its most proximal ring. This tube is used to expand and collapse individual splines. The linked spline assemblies are mounted over a center tube 560 which is affixed at 576 at its distal end to the most distal ring of the spline assembly. By pushing tube 570 distally towards the tip, the spline assemblies are expanded, while pulling tube 570 away from the tip collapses the spline assemblies.

Figure 5B:
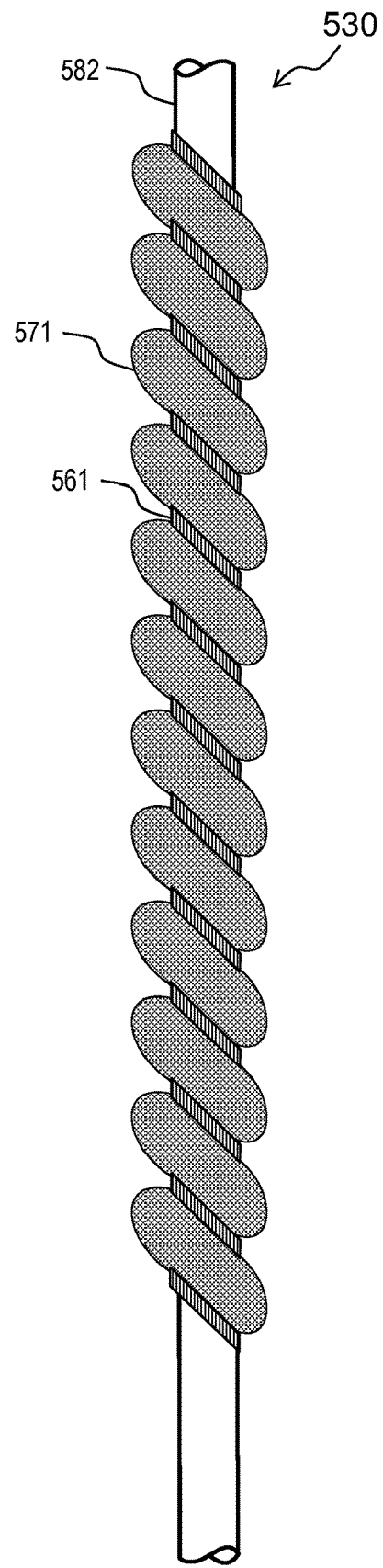
FIG. 5B is a side view of a deflection device 530 using a single balloon 571 that is helically wrapped with a metal strap 561, according to some embodiments of the present invention.

FIG. 5B is a side view of a deflection device 530 using a single balloon 571 that is helically wrapped with a metal strap 561, and in the inflated state, according to some embodiments of the present invention. In some embodiments, a single balloon 571 is used to completely cover the outside of a catheter shaft 582. The balloon 571 is then affixed to catheter shaft 582 in a spiral pattern using a strap 561 (e.g., made of metal or other material) wrapped helically around the balloon 571 and shaft 582, or by adhesive applied to the catheter shaft in a helical pattern (not shown, but where the adhesive functions to replace strap 561), or by thermally bonding the balloon to the catheter shaft 582 in a helical pattern.

FIG. 6A1 is a side view of an expansion catheter 620 using a single balloon 671 wrapped in a spiral pattern around a catheter shaft, shown with balloon 671 deflated, according to some embodiments of the present invention.

FIG. 6A2 is a side view of an expansion catheter 620 using a single balloon 671 wrapped in a spiral pattern around a catheter shaft, shown with balloon 671 inflated, according to some embodiments of the present invention. FIG. 6A1 and FIG. 6A2 illustrate an embodiment of the current invention in which a single balloon is wrapped in a spiral pattern around a catheter shaft. Balloon 671 has a very high L/D ratio compared to the balloons used in FIG. 2A and FIG. 2B. In this embodiment of the present invention, diameters can range from 1.0 to 20.0 mm (0.040 to 0.800 inch), preferably from 3.0 to 8.0 mm (0.118 to 0.320 inch). Balloons can be made of elastic materials such as a soft-durometer polyurethane or silicone. Balloons can also be made of non-compliant materials which have a fixed shape. Typical materials include various durometer nylons, polyethylene terephthalates (PET), polyesters and blends of different polymer families. In some embodiments, the balloon can be thin-walled tubing with a wall thickness ranging from 0.001 to 0.2 mm (0.0004 to 0.008 inch). Depending on the length of the deflection section, the number of spirals the balloon makes around the catheter shaft may vary from more than one (1) spiral to more than thirty (30) spirals, but preferably of the order of ten (10) spirals (or, in other embodiments, about 5, about 15, about 20 or about 25 spirals). Using these ranges, in some embodiments, the L/D ratio of the balloon can vary from a minimum of approximately five (5) to maximum of approximately one hundred or one-hundred fifty or even up to one thousand (1,000) or more.

One difficulty in implementing this concept is a tendency for the balloon to migrate along the length of the catheter shaft and not maintain a uniform threaded screw geometry longitudinally along the catheter shaft. This tendency is more apparent during insertion into a body lumen where there is likely drag along the outer surfaces of the deflated balloon. In order to overcome this tendency, grooves can be located in the catheter shaft to house the deflated balloon.

FIG. 6B1 is a partial longitudinal cross-sectional view of the expansion catheter 620 of FIG. 6A1 along section 6B1-6B1 shown in FIG. 6A1, wherein balloon 671 is in the deflated state.

FIG. 6B2 is a partial longitudinal cross-sectional view of the expansion catheter 620 of FIG. 6A2 along section 6B2-6B2 shown in FIG. 6A2, wherein balloon 671 is in the inflated state. In some embodiments, helical groove 686 is embossed or imprinted in the outside of catheter shaft 612. Deflated balloon 671 is contained either partially or fully (as shown) within the confines of the groove.

Another embodiment of the present invention is shown in FIG. 6C. Balloons 170 are attached to catheter surface 112 such that the catheter shaft passes along the outside surface of balloons 170. When the balloons are expanded, catheter shaft 112 is pushed against a side of a body lumen, achieving the aforementioned effect of fixing the relationship between a catheter shaft and an expanded body lumen. One disadvantage to this embodiment is the expansion means must be released and returned to its natural position in order to repositioned the expansion catheter.

FIG. 6D1 is a side-view of an expansion catheter 640, with a single balloon 670 in a deflated state, in which a catheter shaft 621 passes through the center of the balloon 670 in a neutral undeflected configuration, according to some embodiments of the present invention.

FIG. 6D2 is a side-view of expansion catheter 640, with single balloon 670 in an inflated state and undeflected neutral configuration, according to some embodiments of the present invention.

FIG. 6D3 is a side-view of expansion catheter 640, with single balloon 670 in an inflated state, in which a catheter shaft 621 passes through the interior of the balloon 670 in a deflected configuration, according to some embodiments of the present invention.

The embodiment of the present invention shown in FIG. 6D1, FIG. 6D2 and FIG. 6D3, includes a single balloon shown in deflated state with no deflection in FIG. 6D1, in an expanded state with no deflection in FIG. 6D2 and an expanded state with deflection in FIG. 6D3. A single balloon 670 is joined to catheter shaft 67 112 at joints 172 such that the catheter shaft passes through the interior of balloon 170. FIG. 6D1 shows the balloon in a deflated state. FIG. 6D2 shows the balloon in an expanded state to engage a body lumen. FIG. 6D3 shows the catheter shaft deflected by a mechanical means such that the catheter shaft moves to the outside of the deflected curve and rests against the concave interior surface of a body lumen fixing the relationship between a catheter shaft and an expanded body lumen and displacing the body lumen laterally resulting in the catheter being curved from its neutral state.

FIG. 6D4 is a side-view of an expansion catheter 650, with a single balloon 680 in a deflated state, in which a catheter shaft 623 is adhered along the side of the balloon 680 in a neutral and a deflected configuration, according to some embodiments of the present invention.

FIG. 6D5 is a side-view of expansion catheter 650, in which catheter shaft 623 in its undeflected neutral configuration is adhered along the side of the balloon 680, which is in an inflated state, according to some embodiments of the present invention.

FIG. 6D6 illustrates expansion catheter 650, with single balloon 680 in an inflated state, in which catheter shaft 623 is in a deflected configuration is adhered along the side of the balloon 680, which is according to some embodiments of the present invention.

The embodiment of the present invention shown in FIG. 6D4, FIG. 6D5 and FIG. 6D6 includes a single balloon shown in deflated state with no deflection, in an expanded state with no deflection and an expanded state with deflection. A single balloon 170 is joined to catheter outer surface 112 of catheter shaft 121 at joints 172 such that the catheter shaft passes along the outside of balloon 170. FIG. 6D4 shows the balloon in a deflated state. FIG. 6D5 shows the balloon in an expanded state to engage a body lumen. FIG. 6D6 shows the catheter shaft deflected by a mechanical means such the body lumen is displaced laterally resulting in the catheter being curved from its neutral state.

In one embodiment of the current invention, an expansion catheter includes an outer tube into which is placed an inner tube to simulate a multi-lumen tube. The outer tube is an extruded nylon, such as Pebax™ 7233, with an outer diameter of 3.17 mm (0.125 inch), an inner diameter of 2.51 mm (0.100 inch), and a calculated wall thickness of 0.33 mm (0.013 inches). The inner tube is an extruded nylon, such as Pebax™ 7233, with an outer diameter of 2.33 mm OD (0.092 inch), an inner diameter of 1.90 mm ID (0.075 inch), and a calculated wall thickness of 0.22 mm (0.008 inch). The inner tube slips inside the outer tube with a clearance between the two tubes of 0.09 mm (0.0035 inch). The two tubes are bonded at their distal ends with an adhesive, Loctite™ 4014, operably sealing the annular gap. The inner tube also has a lubricious coating on its inside surface to facilitate insertion of a guidewire and deflection mechanism during operation.

In one embodiment of the present invention, the expansion catheter includes fives balloons bonded to the outer tube using Dymax UV Adhesive 1161-M. Each balloon is made of soft polyurethane which can be expanded up to a working diameter of 2.54 cm (1.00 inch). The balloons are 5.0 cm (1.96 inch) long including necks. In the bonded area, the outer diameter of the bond is 3.8 mm (0.150 inches). The length of the deflected section—the distance from the distal edge of the most distal balloon to the proximal edge of the most proximal balloon—is 25.4 cm (10.0 inch). A skive in the outer shaft is located within each balloon to connect the interior of the balloon with the annular gap in the catheter shaft between the inner and outer tube. This configuration has a single lumen connecting all balloons so that the balloons are inflated/deflated simultaneously.

In one embodiment of the current invention, the proximal end of the expansion catheter contains a Y adapter with a single side arm having a female luer connector and Tuohy Borst gasket with a threaded cap. The Y adapter is bonded to both the inner and outer tube of the catheter shaft to operably couple the annular channel to the side arm of the Y adapter. The Tuohy Borst functions as an entrance to the central lumen of the expansion catheter for slideably accommodating a guidewire and a deflection mechanism and as a fixation device for locking the position of the deflection mechanism within the expansion catheter during operation.

In one embodiment of the present invention, a deflection mechanism includes a column made from a hypodermic tube with an outer diameter of 1.83 mm (0.072 inch), an inner diameter of 1.6 mm (0.063 inch), and a length of 25.4 cm (10 inch). An adapter which interfaces with the hypodermic tube and the leaf-spring assembly contains three drilled holes, two of which are adjacent to each other with a third centered below these two holes. The overall diameter of the adapter is 1.88 mm (0.074 inch).

In one embodiment of the current invention, two round wires are used to form a leaf spring. Each wire is made of Nitinol with a diameter of 0.81 mm (0.032 inch) a length of 17 mm (6.7 inch). The Nitinol wires are soldered into the adapter with a suitable flux and solder. An adapter similar to the one described above but with two holes is soldered onto the distal end of the longer Nitinol wire.

In one embodiment of the current invention, a tensioning wire used for the curving of the leaf spring is made from a braided stainless steel wire with an outer diameter of 0.32 mm (0.013 inch). The distal end of the wire is soldered into the distal adapter at the end of the longer Nitinol wire. The wire is then passed thru the proximal adapter and soldered into a small heavy wall hypodermic tube which is then fixated within the handle.

In one embodiment of the current invention, a handle includes a nut and a threaded rod to move the tensioning wire longitudinally. The threaded rod is configured so that it cannot rotate but can move laterally due to a slot in the threaded rod that contains a set screw that fits into the handle. The set-screw is loose enough to allow axial movement but prevent rotation.

In one embodiment of the current invention, with the deflection mechanism in its neutral or straight state, deflection occurs by rotating the knob in the handle in a specific direction, causing the threaded rod to advance distally toward the tip of the deflection mechanism. This simultaneously advances the column connected to the threaded rod. Because the tensioning wire is anchored at the distal end of the leaf-spring assembly and the back of the handle, the distance between the endpoints of the leaf-spring assembly is operably shortened, causing the leaf-spring assembly to deflect in its structurally most flexible plane. Reversing the direction of rotation of the knob lengthens the distance between the endpoints of the leaf-spring assembly, allowing the assembly to return to a more neutral state and ultimately to its resting state.

In one embodiment of the current invention, a deflection, $D_y$, of approximately 5 cm is obtained over a distance $L_x$ of approximately 24 cm.

In some embodiments, the present invention provides a deflection catheter for displacing a portion of an internal passageway of a body lumen. This deflection catheter includes: a catheter shaft having a distal end and proximal end containing at least one lumen therein over at least a portion of length of said catheter shaft; an expandable set of balloon members affixed to the catheter shaft along at least a portion of said catheter shaft; each balloon member sealably affixed to the catheter shaft on both its distal and proximal ends such that the interior space of each balloon is operably coupled to at least one lumen within said catheter shaft; and a deflection mechanism contained within at least one lumen of said catheter shaft and operably coupled to said catheter shaft, such that a change in shape of the deflection mechanism causes a corresponding change in shape of said catheter shaft along at least a portion of said catheter shaft which contains at least one balloon.

In some embodiments, the present invention provides a deflection catheter for displacing a portion of an internal passageway of a body lumen. This deflection catheter includes: a catheter shaft having a distal end and proximal end containing at least a first lumen therein over at least a portion of length of said catheter shaft; one or more expandable members affixed to the catheter shaft along at least a portion of said catheter shaft; each expandable member sealed to the catheter shaft on both a distal end of the expandable member and a proximal end of the expandable member such that an interior space of each balloon is operably coupled to first lumen within said catheter shaft; and a deflection mechanism contained within at least one lumen of said catheter shaft and operably coupled to said catheter shaft, such that a change in shape of the deflection mechanism causes a corresponding change in shape of said catheter shaft along at least a portion of said catheter shaft which contains at least one balloon.

In some embodiments, the one or more expandable members comprises a plurality of at least five balloons spaced along a length of the catheter shaft, the deflection mechanism is removably insertable into a second lumen in the catheter shaft, the deflection mechanism includes a deflection portion between a proximal end and a distal end of the deflection mechanism, the deflection portion changes a radius of curvature in a deflection plane upon application of a axial force on the deflection mechanism, and the deflection mechanism includes a Tuohy Borst clamping mechanism operable to lock the deflection mechanism at a selected angle of a plurality of available angles in order to set an orientation of the deflection plane's direction (i.e., the direction toward which the expandable diverter will move the target lumen).

In some embodiments, the present invention provides an apparatus for displacing a portion of a body lumen. This apparatus includes: a shaft; a first lumen within the shaft extending over at least a portion of length of the apparatus; an expandable member attached to the shaft and configured to expand within the body lumen; and a deflection mechanism located within the first lumen and configured to change shape by lateral deflection to cause a corresponding lateral deflection of the shaft along at least a portion of the shaft attached to the expandable member.

In some embodiments, the shape change by lateral deflection is a result of a change in a radius of curvature of the deflection mechanism. In some embodiments, the shape change by lateral deflection is caused by applying tension to a portion of the deflection mechanism Some embodiments further include a tube operatively coupled to the expandable member to inject a fluid into the expandable member to cause the expandable member to expand within the body lumen.

Some embodiments further include a second lumen within the shaft that is operatively coupled to the expandable member to inject a fluid into the expandable member to cause the expandable member to expand within the body lumen.

In some embodiments, the first lumen within the shaft is operatively coupled to the expandable member to inject a fluid into the expandable member to cause the expandable member to expand within the body lumen.

In some embodiments, the expandable member includes a plurality of expandable segments serially located along the shaft, wherein each one of the plurality of expandable segments surrounds the shaft such that when each one of the plurality of expandable segments of the expandable member expands within the body lumen, the shaft is substantially centered within each one of the plurality of expandable segments.

In some embodiments, the deflection mechanism includes a plurality of flat side-by-side metal segments of different lengths and a contraction cable configured to cause a curve in the plurality of flat side-by-side metal segments when the cable is placed in tension.

In some embodiments, the present invention provides a positioning device configured for introduction within a body lumen. This positioning device includes: a catheter shaft that has a longitudinal axis; an expandable element coupled along a length of the shaft, the expandable element being substantially flaccid in an unexpanded state and having a limited maximum diameter in an expanded state; and a deflection mechanism located within the shaft, wherein the deflection mechanism is flexible when in a non-deflected state and wherein the deflection mechanism curves in a predetermined lateral direction when in a deflected state such that the positioning device laterally deflects the body lumen.

In some embodiments, the present invention provides a method for displacing a portion of a body lumen. This lumen-displacement method includes: providing a shaft having a first lumen within the shaft, the lumen extending through at least a portion of length of the shaft, an expandable member attached to the shaft, and a deflection mechanism within the first lumen; inserting the shaft into a body lumen of an animal; expanding the expandable member within the body lumen of the animal; and changing a shape of the deflection mechanism by lateral deflection to cause a corresponding lateral deflection of the body lumen of the animal. In some embodiments, the animal is a human.

In some embodiments, the present invention provides an apparatus for displacing a portion of a flexible target lumen. This apparatus includes: a catheter shaft having a first catheter-shaft lumen within the catheter shaft, the first catheter-shaft lumen extending through at least a portion of length of the catheter shaft; a plurality of inflatable and deflatable balloons located along the catheter shaft and operably coupled to the first catheter-shaft lumen and configured to expand in diameter within the flexible target lumen to form an expanded first portion of the apparatus; and a lateral deflection mechanism operably coupled to the catheter shaft and configured to laterally deflect the expanded first portion of the apparatus while within the flexible target lumen in order to laterally deflect the flexible target lumen.

Some embodiments further include a guidewire to guide at least a portion of the catheter shaft into the flexible target lumen.

Some embodiments further include a guidewire to guide at least a portion of the catheter shaft into the flexible target lumen; and a second catheter-shaft lumen in the catheter shaft, wherein the guidewire is removably insertable into the catheter-shaft second lumen, and wherein the lateral deflection mechanism is removably insertable into the second catheter-shaft lumen.

Some embodiments further include a second catheter-shaft lumen in the catheter shaft, wherein the guidewire is removably insertable into the catheter-shaft second lumen, and wherein the lateral deflection mechanism is removably insertable into the second catheter-shaft lumen.

In some embodiments, the present invention provides an apparatus for displacing a portion of a flexible target lumen. This apparatus includes: a catheter shaft having a first catheter-shaft lumen within the catheter shaft, the first catheter-shaft lumen extending through at least a portion of length of the catheter shaft; means for expanding a diameter of a first portion of the apparatus when the apparatus is, at least partially, within the flexible target lumen, wherein the means for expanding the diameter of the first portion of the apparatus is operably coupled to the first catheter-shaft lumen; and means for laterally deflecting the expanded first portion of the apparatus while within the flexible target lumen in order to deflect the flexible target lumen. Some embodiments further include means for guiding at least a portion of the catheter shaft into the flexible target lumen. Some embodiments further include means for guiding at least a portion of the catheter shaft into the flexible target lumen; and a second catheter-shaft lumen in the catheter shaft, wherein the means for guiding is removably insertable into the catheter-shaft second lumen, and wherein the means for laterally deflecting the expanded portion of the apparatus within the flexible target lumen is removably insertable into the second catheter-shaft lumen. Some embodiments further include a second catheter-shaft lumen in the catheter shaft, wherein the means for laterally deflecting the expanded portion of the apparatus within the flexible target lumen is removably insertable into the second catheter-shaft lumen.

In some embodiments, the present invention provides an apparatus for displacing a portion of a body lumen. This apparatus includes a shaft; a first lumen within the shaft extending over at least a portion of length of the apparatus; an expandable member attached to the shaft and configured to expand within the body lumen; and a deflection mechanism located within the first lumen and configured to change shape by lateral deflection to cause a corresponding lateral deflection of the shaft along at least a portion of the shaft attached to the expandable member.

In some embodiments, the present invention provides an apparatus for displacing a portion of a body lumen. This apparatus includes: a shaft; a first lumen within the shaft extending over at least a portion of length of the apparatus; an expandable member attached to the shaft and configured to expand within the body lumen; and a deflection mechanism located within the first lumen and configured to change shape by lateral deflection to cause a corresponding lateral deflection of the body lumen. Some embodiments further include a tube operatively coupled to the expandable member to inject a fluid into the expandable member to cause the expandable member to expand within the body lumen. Some embodiments further include a second lumen within the shaft and operatively coupled to the expandable member to inject a fluid into the expandable member to cause the expandable member to expand within the body lumen. In some embodiments, the first lumen within the shaft is operatively coupled to the expandable member to inject a fluid into the expandable member to cause the expandable member to expand within the body lumen. In some embodiments, the expandable member includes a plurality of expandable segments serially located along the shaft, wherein each one of the plurality of expandable segments surrounds the shaft such that when each one of the plurality of expandable segments of the expandable member expands within the body lumen, the shaft is substantially centered within each one of the plurality of expandable segments. In some embodiments, the deflection mechanism includes a plurality of flat side-by-side metal segments of different lengths and a contraction cable configured to cause a curve in the plurality of flat side-by-side metal segments when the cable is placed in tension.

In some embodiments, the present invention provides a positioning device configured for introduction within a body lumen. This device includes: a shaft with a longitudinal axis; an expandable element coupled along a length of the shaft, the expandable element being substantially flexible and thin in an unexpanded state, and exerting a gentle outward force in an expanded state; and a deflection mechanism located within the shaft, wherein the deflection mechanism is flexible when in a non-deflected state and wherein the deflection mechanism curves in a predetermined lateral direction when in a deflected state such that the positioning device laterally deflects the body lumen.

In some embodiments, the present invention provides a method for displacing a portion of a body lumen, the method including: providing a shaft having a first lumen within the shaft, the lumen extending through at least a portion of length of the shaft, an expandable member attached to the shaft, and a deflection mechanism within the first lumen; inserting the shaft into a body lumen of an animal; expanding the expandable member within the body lumen of the animal; changing a shape of the deflection mechanism by lateral deflection to cause a corresponding lateral deflection of the body lumen of the animal. In some embodiments, the animal is a human. In some embodiments, the deflection mechanism is inserted into the first lumen after the shaft has been inserted into the body lumen of the animal.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus for displacing a portion of a body lumen, the apparatus comprising:
   a shaft;
   a first lumen within the shaft extending over at least a portion of length of the apparatus;
   an expandable member attached to the shaft and configured to expand within the body lumen; and
   a deflection mechanism configured to be inserted into the first lumen to a desired depth of the first lumen and to change shape by lateral deflection to cause a corresponding lateral deflection of the body lumen, wherein, when the deflection mechanism is in its undeflected neutral configuration, a distal portion of the deflection mechanism is along a first line defined between a proximal portion of the deflection mechanism and the distal portion, and wherein, when the deflection mechanism is changed in shape to a deflected configuration, a deflected portion of the deflection mechanism between the distal portion and the proximal portion curves away from the first line and then curves back toward the first line while the distal portion and the proximal portion are along the first line, wherein the deflection mechanism includes a plurality of flat side-by-side metal segments of different lengths and a contraction cable configured to cause a curve in the plurality of flat side-by-side metal segments when the cable is placed in tension.

2. An apparatus for displacing a portion of a body lumen, the apparatus comprising:
   a shaft;
   a first lumen within the shaft extending over at least a portion of length of the apparatus;
   an expandable member attached to the shaft and configured to expand within the body lumen; and
   a deflection mechanism configured to be inserted into the first lumen to a desired depth of the first lumen and to change shape by lateral deflection to cause a corresponding lateral deflection of the body lumen, wherein, when the deflection mechanism is in its undeflected neutral configuration, a distal portion of the deflection mechanism is along a first line defined between a proximal portion of the deflection mechanism and the distal portion, and wherein, when the deflection mechanism is changed in shape to a deflected configuration, a deflected portion of the deflection mechanism between the distal portion and the proximal portion curves away from the first line and then curves back toward the first line while the distal portion and the proximal portion are along the first line, wherein the expandable member surrounds the shaft such that at least a portion of the expandable member surrounds at least a part of the deflected portion of the deflection mechanism, wherein the deflection mechanism is further configured to rotate circumferentially within the shaft.

3. The apparatus of claim 2, further comprising a tube operatively coupled to the expandable member to inject a fluid into the expandable member to cause the expandable member to expand within the body lumen.

4. The apparatus of claim 2, further comprising a second lumen within the shaft and operatively coupled to the expandable member to inject a fluid into the expandable member to cause the expandable member to expand within the body lumen.

5. The apparatus of claim 2, wherein the first lumen within the shaft is operatively coupled to the expandable member to inject a fluid into the expandable member to cause the expandable member to expand within the body lumen.

6. The apparatus of claim 2, wherein the expandable member includes a plurality of expandable segments serially located along the shaft, wherein each one of the plurality of expandable segments surrounds the shaft such that when each one of the plurality of expandable segments of the expandable member expands within the body lumen, the shaft is substantially centered within each one of the plurality of expandable segments.

7. The apparatus of claim 2, further comprising:
   a guidewire configured to guide at least a portion of the shaft into the body lumen.

8. An apparatus for displacing a portion of a flexible target lumen, the apparatus comprising:
   a catheter shaft having a first catheter-shaft lumen within the catheter shaft, the first catheter-shaft lumen extending through at least a portion of a length of the catheter shaft;
   means for expanding a diameter of a first portion of the apparatus when the apparatus is, at least partially, within the flexible target lumen, wherein the means for expanding the diameter of the first portion of the apparatus is operably coupled to the first catheter-shaft lumen; and
   means for laterally deflecting the expanded first portion of the apparatus while within the flexible target lumen in order to deflect the flexible target lumen, wherein the means for laterally deflecting is configured to move longitudinally within the catheter shaft to a desired depth of the catheter shaft while the means for expanding is expanded, in order to alter a longitudinal location of an entire deflected portion of the catheter shaft, wherein at least a portion of the means for expanding surrounds at least a part of the deflected portion of the catheter shaft, wherein the means for laterally deflecting is configured to rotate circumferentially within the catheter shaft.

9. The apparatus of claim 8, further comprising: means for guiding at least a portion of the catheter shaft into the flexible target lumen.

10. The apparatus of claim 8, further comprising:
means for guiding at least a portion of the catheter shaft into the flexible target lumen; and
a second catheter-shaft lumen in the catheter shaft, wherein the means for guiding is removably insertable into the catheter-shaft second lumen, and wherein the means for laterally deflecting the expanded portion of the apparatus within the flexible target lumen is removably insertable into the second catheter-shaft lumen.

11. The apparatus of claim 8, further comprising:
a second catheter-shaft lumen in the catheter shaft, wherein the means for laterally deflecting the expanded portion of the apparatus within the flexible target lumen is removably insertable into the second catheter-shaft lumen.

12. The apparatus of claim 8, wherein the means for expanding the diameter of the first portion of the apparatus includes means for injecting a fluid into the means for expanding the diameter of the first portion of the apparatus.

13. The apparatus of claim 8, further comprising a second catheter-shaft lumen in the catheter shaft, wherein the second catheter-shaft lumen is operably coupled to the means for expanding in order to inject a fluid into the means for expanding to cause the means for expanding to expand within the flexible target lumen.

14. A method for displacing a portion of a body lumen, the method comprising:
providing a shaft having a first lumen within the shaft, the lumen extending through at least a portion of a length of the shaft, an expandable member attached to the shaft, and a deflection mechanism that can be moved longitudinally within the first lumen;
inserting the shaft into a body lumen of an animal;
expanding the expandable member within the body lumen of the animal;
changing a shape of the deflection mechanism by lateral deflection to form a deflected portion of the shaft and cause a corresponding lateral deflection of the body lumen of the animal; and
moving the deflection mechanism longitudinally within the first lumen to a desired depth of the first lumen in order to alter a longitudinal location of the entire deflected portion of the shaft, wherein the deflection mechanism includes a plurality of flat side-by-side metal segments of different lengths, wherein the changing of the shape of the deflection mechanism includes causing a curve in the plurality of flat side-by-side metal segments.

15. An apparatus for displacing a portion of a body lumen, the apparatus comprising:
a shaft;
a first lumen within the shaft extending over at least a portion of length of the apparatus; an expandable member attached to the shaft and configured to expand within the body lumen; and
a deflection mechanism configured to be inserted into the first lumen to a desired depth of the first lumen and to change shape by lateral deflection to cause a corresponding lateral deflection of the body lumen, wherein, when the deflection mechanism is in its undeflected neutral configuration, a distal portion of the deflection mechanism is along a first line defined between a proximal portion of the deflection mechanism and the distal portion, and wherein, when the deflection mechanism is changed in shape to a deflected configuration, a deflected portion of the deflection mechanism between the distal portion and the proximal portion curves away from the first line and then curves back toward the first line while the distal portion and the proximal portion are along the first line, wherein the deflection mechanism includes a plurality of flat metal segments of different lengths that are arranged face-to-face, and a contraction cable configured to cause a curve in the plurality of flat metal segments when the cable is placed in tension, wherein a first metal segment of the plurality of flat metal segments has a longest length of the plurality of flat metal segments, wherein a distal end of the contraction cable is attached to the first metal segment, and wherein at least a second metal segment of the plurality of flat metal segments is located between the first metal segment and the contraction cable.

16. A method for displacing a portion of a body lumen, the method comprising:
providing a shaft having a first lumen within the shaft, the lumen extending through at least a portion of a length of the shaft, an expandable member attached to the shaft, and a deflection mechanism that can be moved longitudinally within the first lumen;
inserting the shaft into a body lumen of an animal;
expanding the expandable member within the body lumen of the animal;
changing a shape of the deflection mechanism by lateral deflection to form a deflected portion of the shaft and cause a corresponding lateral deflection of the body lumen of the animal;
moving the deflection mechanism longitudinally within the first lumen to a desired depth of the first lumen in order to alter a longitudinal location of the entire deflected portion of the shaft, wherein at least a portion of the expandable member surrounds at least a part of the deflected portion of the shaft; and
rotating the deflection mechanism circumferentially within the first lumen to a desired circumferential location.

17. The method of claim 16, wherein the animal is a human.

18. The method of claim 16, wherein the shaft includes a second lumen within the shaft, the method further comprising:
removing the deflection mechanism from the first lumen and inserting the deflection mechanism into the second lumen.

19. The method of claim 16, wherein the expanding of the expandable member includes injecting a fluid into the expandable member.

20. The method of claim 16, wherein the shaft includes a second lumen within the shaft, and wherein the expanding of the expandable member includes injecting a fluid into the expandable member via the second lumen.

21. The method of claim 16, wherein the expandable member includes a plurality of expandable segments serially located along the shaft, wherein each one of the plurality of expandable segments surrounds the shaft such that when each one of the plurality of expandable segments of the expandable member expands within the body lumen, the shaft is substantially centered within each one of the plurality of expandable segments.

22. The method of claim 16, further comprising:
providing a guidewire, wherein the inserting of the shaft into the body lumen includes guiding the shaft into the body lumen using the guidewire.

* * * * *